United States Patent [19]

Ichijima et al.

[11] Patent Number: 4,818,668
[45] Date of Patent: Apr. 4, 1989

[54] SILVER HALIDE COLOR PHOTOGRAPHIC MATERIALS

[75] Inventors: Seiji Ichijima; Hideo Usui; Kohzaburoh Yamada, all of Kanagawa, Japan

[73] Assignee: Fuji Photo Film Co., Ltd., Kanagawa, Japan

[21] Appl. No.: 56,280

[22] Filed: May 26, 1987

Related U.S. Application Data

[63] Continuation of Ser. No. 769,049, Aug. 26, 1985, abandoned.

[30] Foreign Application Priority Data

Aug. 24, 1984 [JP] Japan ................ 59-176353

[51] Int. Cl.⁴ .............................. G03C 1/40
[52] U.S. Cl. .................... 430/505; 430/553; 430/549
[58] Field of Search .............. 430/553, 549, 505

[56] References Cited

U.S. PATENT DOCUMENTS

| | | |
|---|---|---|
| 3,476,563 | 11/1969 | Loria ................................ 430/553 |
| 4,052,212 | 10/1967 | Deguchi et al. ............... 430/553 |
| 4,401,752 | 8/1983 | Lau .................................. 430/553 |
| 4,532,202 | 7/1985 | Sasaki et al. .................. 430/553 |
| 4,537,857 | 8/1985 | Takada et al. ................. 430/553 |
| 4,543,323 | 9/1985 | Iijima et al. .................... 430/553 |
| 4,551,442 | 11/1985 | Kimura et al. ................. 430/553 |

FOREIGN PATENT DOCUMENTS

| | | | |
|---|---|---|---|
| 3429257 | 2/1985 | Fed. Rep. of Germany ...... | 430/553 |
| 59-111643 | 6/1984 | Japan ................ | 430/553 |
| 59-111644 | 6/1984 | Japan ................ | 430/553 |
| 60-49336 | 3/1985 | Japan ................ | 430/553 |

*Primary Examiner*—Won H. Louie
*Attorney, Agent, or Firm*—Sughrue, Mion, Zinn, Macpeak & Seas

[57] ABSTRACT

A silver halide color photographic light-sensitive material is described, containing at least one coupler represented by formula (I)

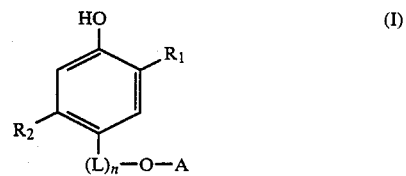

wherein $R_1$ represents a substituted or unsubstituted ureido group or a substituted or unsubstituted acrylamino group; $R_2$ represents substituted or unsubstituted acylamino group; L represents a group which is capable of being released from the phenolic group of formula (I) in a reaction with the oxidation product of a developing agent, and releases -O-A thereafter; n represents 0 or 1; and A represents an aromatic group including a hydroxy group or a substituted or unsubstituted amino group at least one of the 2-position and the 4-position thereof.

31 Claims, No Drawings

4,818,668

SILVER HALIDE COLOR PHOTOGRAPHIC MATERIALS

This is a continuation of application Ser. No. 769,049, filed Aug. 26, 1985, now abandoned.

FIELD OF THE INVENTION

This invention relates to a silver halide color photographic material providing color images having excellent quality, particularly having excellent graininess and sharpness properties, and showing less dark heat fading (fading in dark-heat place), by the incorporation of a novel cyan coupler.

BACKGROUND OF THE INVENTION

A dye cloud constituting a color image in subtractive color process-color photography is formed by a coupling reaction of the oxidation product of a developing agent formed during color development and a coupler. In this case, if the diffusion of the oxidation product of a developing agent is large, the dye cloud becomes large to form a mottled image (i.e., mottles), and resulting in deterioration of the graininess properties.

Various means for preventing the diffusion of the oxidation product of a developing agent for overcoming the above-described defects have been proposed.

For example, examples of a coupler blocked by a water-soluble coupler are disclosed in U.S. Pat. No. 4,310,618. Also, examples of couplers releasing diffusible couplers are described in *Research Disclosure*, RD No. 19633 (August, 1980) and U.S. Pat. No. 4,130,427. However, these known couplers are not totally satisfactory in the effect of controlling the gradation and the effect of improving the graininess, although they show these weak effects. Also, there is a problem of color turbidity as a fundamental defect of the releasing coupler type compound. That is, in the case of using such a compound, it is required to provide sufficient diffusibility of the dye formed by the coupling reaction of the compound to flow in a developer, but in this case, the effect of improving the graininess by the compound is reduced. This discrepancy is unavoidable.

Recently, couplers releasing an electron donor compound have been disclosed in Japanese Patent Application (OPI) No. 138,636/'82 (the term "OPI" as used herein refers to a "published unexamined Japanese patent application"). However, these coupler caused various problems, such as that the coupling speed is low, which causes a problem for practical use of the compound, or the coupler residue (i.e., the structure of the other moiety (not the electron donor moiety) constituting the dye-forming moiety) has a problem, in that color images formed are poor in dark heat fading resistance property. More particularly, such cyan couplers for a red-sensitive silver halide emulsion layer have a severe problem, in that when a coupler residue showing a high coupling speed is used, the resistance to dark heat fading is poor, while when the coupler residue having good resistance to dark heat fading is used, the coupling speed is low.

Known cyan coupler residues having good dark heat fading resistance are described, for example, in U.S. Pat. Nos. 4,333,999; 4,299,914; 4,012,258, etc. However, in the case of using these known two-equivalent cyan couplers having these coupler residues, a sufficient coupling speed is not obtained.

SUMMARY OF THE INVENTION

The above-described problems have been overcome by this invention.

That is, an object of this invention is to provide a silver halide color photographic material providing color images having excellent graininess and sharpness properties, and showing less dark heat fading of cyan images. This is achieved according to this invention by employing a novel cyan coupler capable of forming cyan dye images by undergoing a coupling reaction with the oxidation product of a developing agent, and thereafter releasing a compound capable of causing an oxidation reduction reaction with the oxidation product of developing agent.

More particularly, it has now been discovered that the above-described object can be attained by a silver halide color photographic material containing at least one coupler represented by formula (I)

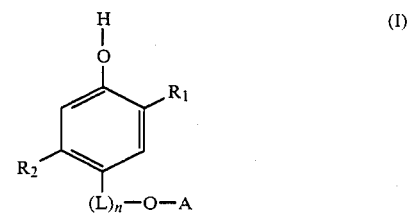

wherein $R_1$ represents a substituted or unsubstituted ureido group or a substituted or unsubstituted acylamino group; $R_2$ represents a substituted or unsubstituted acylamino group; L represents a group which is capable of being released from the phenolic group of formula (I) in a reaction with the oxidation product of a developing agent, and releases —O—A thereafter; n represents 0 or 1; and A represents an aromatic group including a hydroxy group or a substituted or unsubstituted amino group at at least one of the 2-position and the 4-position thereof.

DETAILED DESCRIPTION OF THE INVENTION

The couplers represented by formula (I) are explained in more detail below.

When $R_1$ in formula (I) represents a substituted ureido group, said $R_1$ of formula (I) is preferably represented by formula (II-a) or (II-b)

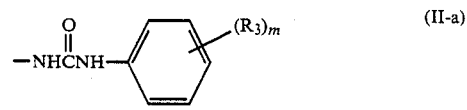

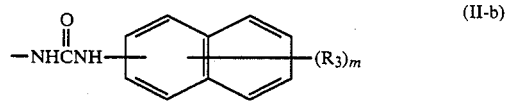

wherein $R_3$ represents an aliphatic group, an aromatic group, a halogen atom, an alkoxy group, an aryloxy group, an acylamino group, an alkoxycarbonyl group, an acylamino group, an alkoxycarbonyl group, an aryloxycarbonyl group, a cyano group, a nitro group, a sulfonyl group, a sulfamoyl group, a carbamoyl group, a ureido group, a carboxyl group, a hydroxyl group, a nitroso group, an alkylthio group, an arylthio group, an acyl group, a sulfonamido group, an acyloxy group, a heterocyclic group, an alkoxycarbonylamino group, an oxamoyl group, a thioacyl group, an acylcarbamoyl group, a sulfinyl group, a thioureido group, a thiocarbamoyl group, a diacylamino group, or an amino group. Each of these groups may be further substituted. Also, m in the above formulae (II-a) and (II-b) represents an integer of 0 to 5 and when m is 2 or more, the $R_3$ groups may be the same or different. When $R_3$ contains an aliphatic moiety, the number of carbon atom of the aliphatic moiety is from 1 to 32, preferably from 1 to 16 and the aliphatic moiety may be a cyclic or non-cyclic moiety, a straight chain or branched chain moiety, a saturated or unsaturated moiety, or a substituted or unsubstituted moiety. When $R_3$ contains an aromatic moiety, the carbon atom number of said aromatic moiety is from 6 to 10 and the aromatic moiety is preferably a substituted or unsubstituted phenyl group. Examples of the substituent for the groups represented by $R_3$ are, preferably, an alkyl group, and more preferably the group represented by $R_1$ and $R_2$ described below.

When $R_1$ or $R_2$ in formula (I) represents an acylamino group, the group is preferably an aliphatic acylamino group or an aromatic acylamino group. When $R_1$ or $R_2$ is an aliphatic acylamino group, the number of carbon atom of the group is from 1 to 32, preferably from 1 to 16, and the aliphatic acylamino group may be from a cyclic or non-cyclic group, a straight chain or branched chain group, a saturated or unsaturated group, and a substituted or unsubstituted group. Preferred examples of the substituents for the group are a halogen atom, an aryloxy group, an arylthio group, an aryloxycarbonyl group, an alkoxycarbonyl group, an acyloxy group, an acylamino group, a sulfonamido group, a hydroxyl group, a carboxyl group, a cyano group, an aryl group, an alkoxy group, an alkylthio group, a carbamoyl group, and a ureido group. When $R_1$ or $R_2$ is an aromatic acylamino group, the number of carbon atoms of the aromatic acylamino group is from 6 to 10, and the group is, preferably, a substituted or unsubstituted phenyl group. Preferred examples of the substituent for the groups are a halogen atom, a sulfonamido group, an alkoxy group, an alkoxycarbonyl group, an aliphatic group, an aryl group, a cyano group, a sulfonyl group, a sulfamoyl group, an acylamino group, a hydroxy group, an alkylthio group, a carbamoyl group, a carboxyl group, and a ureido group.

Also, examples of the connecting group represented by L in formula (I) are a group capable of being cleaved by an intramolecular nucleophilic substitution reaction after being released from the coupler as described in U.S. Pat. No. 4,248,962, Japanese Patent Application (OPI) No. 56,837/82, etc.; a group capable of being cleaved by an electron transfer through a covalent bond as described in British Pat. No. 2,072,363, Japanese Patent Application (OPI) Nos. 154,234/82, 188,035/82, etc.; a methyleneoxy group as described in U.S. Pat. No. 4,146,396; a oxycarbonyloxy group as described in Japanese Patent Application (OPI) No. 146,828/76; and a group capable of being cleaved by an electron transfer through a sigma ($\sigma$) bond as described in Japanese Patent Application Nos. 106,223/84 (corresponding to U.S. patent application Ser. Nos. 737,853 filed on May 28, 1985) and 106,224/84 (corresponding to U.S. patent application Ser. No. 737,636 filed on May 24, 1985).

U.S. Pat. No. 4,248,962 Lau discloses a preferred class of photographic coupler compounds which can be represented by the structure:

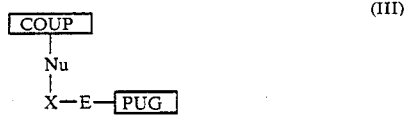

where:
COUP is a coupler moiety, as described above;
PUG is a photographically useful group, as described above;
Nu is a nucleophilic group attached to a position on COUP from which it will be displaced upon reaction of COUP with oxidized color developing agent;
E is an electrophilic group attached to the hetero atom in PUG and is displacable therefrom by Nu after Nu is displaced from COUP; and
X is a linking group for spatially relating Nu and E, upon displacement of Nu from COUP, to undergo an intramolecular nucelophilic displacement reaction with the formation of a three- to seven-membered ring and thereby release PUG.

Representative Nu groups contain electron rich oxygen, sulfur and nitrogen atoms. Representative E groups contain electron deficient carbonyl, thiocarbomyl, phosphinyl and thiophosphinyl moieties. Other useful Nu and E groups will be apparent to those skilled in the art.

In the following listings of representative Nu and E groups, the groups are oriented so that the lefthand bond of Nu is joined to COUP and the righthand bond of Nu is joined to X, while the lefthand bond of E is joined to X and the righthand bond of E is joined to PUG.

Representative Nu groups include:

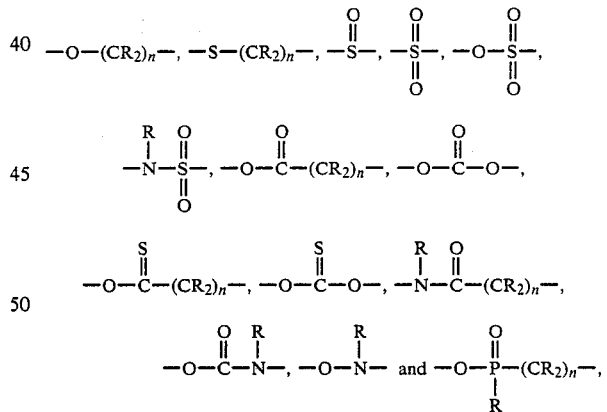

where each R is independently hydrogen, alkyl of 1 to 20 carbon atoms including subtsituted alkyl such as methyl, ethyl, propyl, hexyl, decyl, pentadecyl, octadecyl, carboxyethyl, hydroxypropyl, sulfonamidobutyl and the like, or aryl of 6 to 20 carbon atoms including substituted aryl such as phenyl, naphthyl, benzyl, tolyl, t-butylphenyl, carboxyphenyl, chlorophenyl, hydroxyphenyl and the like, and n is an integer from 0 to 4 such that the ring formed by Nu, X and E upon nucleophilic attack of Nu upon the electrophilic center in E contains 3 to 7 ring atoms. Preferably R is hydrogen, lower alkyl of 1 to 4 carbon atoms or aryl of 6 to 10 carbon atoms.

Representative E groups include:

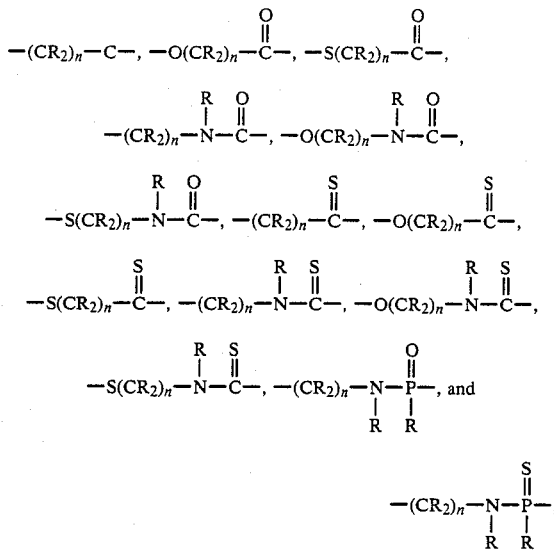

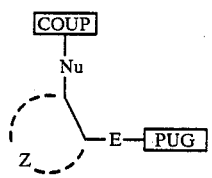

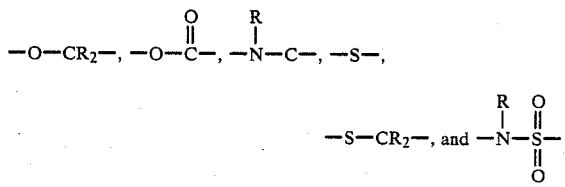

where R and n are defined above.

The linking group represented by X can be an acyclic group such as alkylene (e.g., methylene, ethylene, propylene, etc.) or a cyclic group such as an aromatic group (e.g. phenylene, naphthylene, etc.) or a heterocyclic group (e.g. furan, thiophene, pyridine, quinoline, benzoxazine, etc.). Preferably X is alkylene or arylene. The groups Nu and E are attached to X to provide, upon release of Nu from COUP, favorable spatial relationship for nucleophilic attack of the nucleophilic center in Nu on the electrophilic center in E. When X is a cyclic group, Nu and E can be attached to the same or adjacent rings. Aromatic groups in which Nu and E are attached to adjacent ring positions are particularly preferred X groups.

Particularly preferred couplers of structure II above can be represented by the structure:

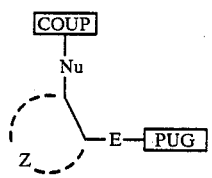
(III)

where:
COUP is a coupler moiety;
Nu is a nucleophilic group attached to the coupling position of COUP, selected from the group consisting of

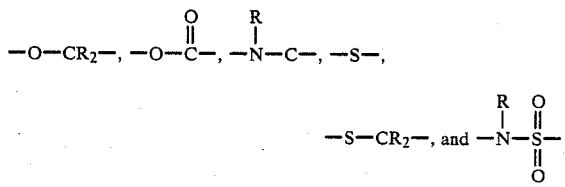

where each R is independently hydrogen, alkyl of 1 to 20 carbon atoms, preferably lower alkyl of 1 to 4 carbon atoms, or aryl of 6 to 20 carbon atoms, preferably aryl of 6 to 10 carbon atoms.

Z represents the atoms necessary to complete a mono- or bicyclic aromatic or heterocyclic ring system, containing 5 to 10 ring atoms, preferably containing ring atoms selected from carbon, oxygen, nitrogen and sulfur;

E is an electrophilic group selected from the group consisting of

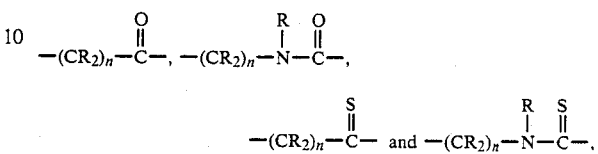

where each R is independently hydrogen, alkyl of 1 to 20 carbon atoms, preferably lower alkyl of 1 to 4 carbon atoms, or aryl of 6 to 20 carbon atoms, preferably aryl of 6 to 10 carbon atoms; and n is an integer of 0 to 4 such that the ring formed upon reaction of the nucleophilic center in Nu with the electrophilic center in E contains 5- to 6-members; and PUG is a photographically useful group containing a hetero atom from Group VA or VIA of the Periodic Table having a negative valence of 2 or 3 through which it is attached to a position in E from which it will be displaced upon nucleophilic attack of Nu at the electrophilic center in E.

In the above structure III the nucleus completed by Z can be unsubstituted or substituted. The substituents can be those which will modify the rate of reaction, diffusion, or displacement, such as halogen (e.g. fluoro, chloro, bromo, iodo), nitro, alkyl of 1 to 20 carbon atoms, acyl (e.g. carboxy, carboxyalkyl, alkoxycarbonyl, alkylcarbonamido, sulfoalkyl, alkylsulfonamido, alkylsulfonyl, etc.), solubilizing groups, ballast groups and the like, or they can be substituents which are separately useful in the photographic element such as a stabilizer, an antifoggant, a dye (e.g., a filter dye, a solubilized masking dye) and the like. For example, solubilizing groups will increase the rate of diffusion; ballast groups will decrease the rate of diffusion; electron withdrawing groups will decrease the rate of displacement of the photographically useful group; and photographically useful groups which remain attached to Z can serve functions such as stabilization, masking and the like.

However, in this invention, these connecting groups may be or may not be used according to the purposes.

The aromatic group represented by A in formula (I) described above has a hydroxyl group or a substituted or unsubstituted amino group at at least one of the 2-position and the 4-position thereof, and may further have other substituents at the other positions. Examples of such a substituent include a halogen atom, an aliphatic group, an aromatic group, a heterocyclic group, an acylamino group, a sulfonamido group, a carbamoyl group, a sulfamoyl group, an acyl group, an alkoxy group, an aryloxy group, an alkylthio group, an arylthio group, a sulfonyl group, a ureido group, a thioacylamino group, a thioureido group, a carboxyl group, a hydroxyl group, and a sulfo group. When the substituent contains an aliphatic moiety, the number of carbon atoms of the moiety is from 1 to 22, preferably from 1 to 8, and the moiety may be a cyclic or noncyclic group, a straight chain or branched chain group, and a saturated or unsaturated group. When the substituent contains an aromatic moiety, the number of carbon atoms of the moiety is from 6 to 10, and the moiety is preferably a substituted or unsubstituted phenyl group.

When at least one of the 2-position and the 4-position of the aromatic group represented by A in formula (I) is a substituted amino group, the substituted amino group preferably includes an aliphatic amino group, an aromatic amino group, an acylamino group, a sulfonamido group, a carbamoylamino group, a sulfamoylamino group, an alkoxyamino group, a hydroxyamino group, and an acyloxyamino group. When the substituted amino group contains an aliphatic moiety, the number of carbon atoms (also referred to herein as the carbon atom number) of the moiety is from 1 to 22, preferably from 1 to 8, and the moiety may be a substituted or unsubstituted group, a cyclic or non-cyclic group, a straight chain or branched group, or a substituted or unsubstituted group. Also, when the substituted amino group contains an aromatic moiety, the number of carbon atoms of the moiety is from 6 to 10, and the moiety is preferably a substituted or unsubstituted phenyl group.

The coupler for use in this invention is preferably used together with other ordinary coupler(s). The ratio of the coupler of this invention/other color image-forming couplers is preferably from 5/95 to 100/0, and more preferably from 10.90 to 60/40.

Examples of couplers which can be used together with the coupler for use in this invention in the same color-sensitive emulsion layer (when the color-sensitive emulsion layer is composed of two or more emulsion layers, these couplers may be in the same emulsion layer or a different emulsion layer) are naphthol cyan couplers and phenol cyan couplers. Particularly preferred couplers which can be used together with the coupler(s) for use in this invention can be represented by formula (III)

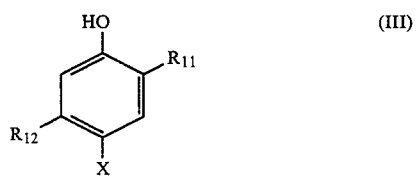

wherein $R_{11}$ and $R_{12}$ have the same meanings as $R_1$ and $R_2$ defined in formula (I) above, respectively and X represents a hydrogen atom or a coupling releasing group.

The coupling releasaing group represented by X in formula (III) is preferably a chlorine atom, an aromatic oxy group, or an aliphatic oxy group.

The aliphatic oxy group represented by X has from 1 to 32 carbon atoms, preferably from 1 to 16 carbon atoms and may be a cyclic or non-cyclic group, a saturated or unsaturated group, a straight chain or branched group, a saturated or unsaturated group, or a substituted or unsubstituted group. Examples of the substituent for the group are a halogen atom, an aryl group, an acylamino group, a carbamoyl group, an alkylthio group, an arylthio group, an alkoxy group, an aryloxy group, a sulfonyl group, a sulfonamido group, a sulfamoyl group, a carboxyl group, a hydroxyl group, a cyano group, a sulfo group, a nitro group, an alkoxycarbonyl group, an aryloxycarbonyl group, an acyl group, an acyloxy group, an imido group, a sulfamoylamino group, a carbamoylamino group, an amino group, a sulfinyl group, a ureido group, an alkoxycarbonylamino group, a carbamoyloxy group, a heterocyclic group, an aromatic group, a hydroxyamino group, a phosphonyl group, and a formyl group. These groups may be further substituted. When the substituent contains an aliphatic moiety, the number of carbon atoms of the moiety is from 1 to 32, and preferably from 1 to 16. When the substituent contains an aromatic moiety, the moiety may be preferably a substituted or unsubstituted phenyl group.

The aromatic oxy group represented by X in formula (III) has from 6 to 10 carbon atoms and is preferably a substituted or unsubstituted phenoxy group. Examples of the substituent for the phenoxy group include a halogen atom, an aliphatic group, an aromatic group, an alkoxy group, an acylamino group, a carbamoyl group, an alkylthio group, an arylthio group, an aryloxy group, a sulfonyl group, a sulfonamido group, a sulfamoyl group, a carboxyl group, a hydroxyl group, a cyano group, a sulfo group, an alkoxycarbonyl group, an aryloxycarbonyl group, an acyl group, an acyloxy group, an imido group, a sulfamoylamino group, a carbamoylamino group, an amino group, a sulfinyl group, a ureido group, an alkoxycarbonylamino group, a carbamoyloxy group, a heterocyclic group, a hydroxyamino group, a phosphonyl group, and a formyl group. These groups may be further substituted. When the substituent contains an aliphatic moiety, the number of carbon atoms of the moiety is from 1 to 32, and preferably from 1 to 16. Also, when the substituent contains an aromatic moiety, the moiety is preferably a substituted or unsubstituted phenyl group.

Specific examples of the compounds (i.e., the couplers) for use in this invention are shown below, but do not limit this invention in any way.

Examples of couplers represented by formula (I)

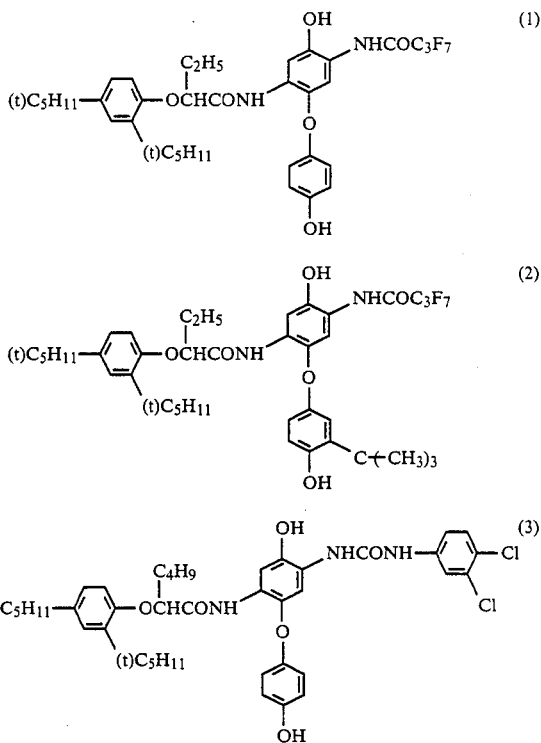

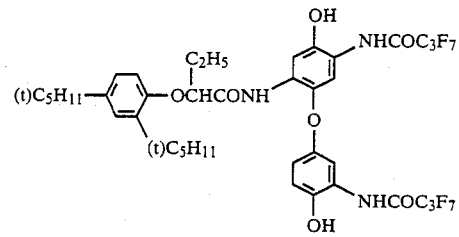 (4)
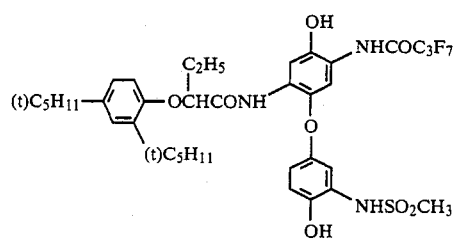 (5)
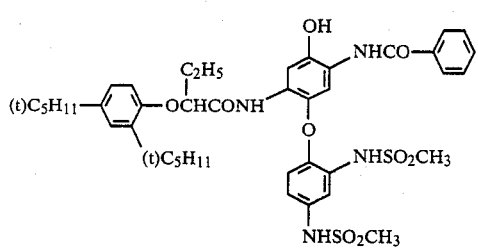 (6)
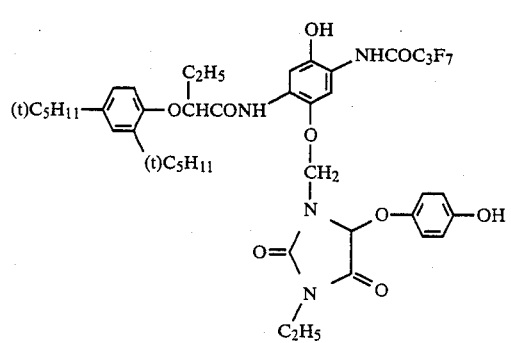 (7)
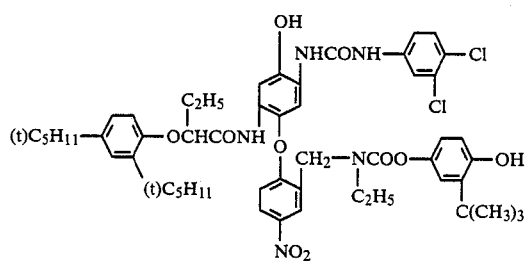 (8)
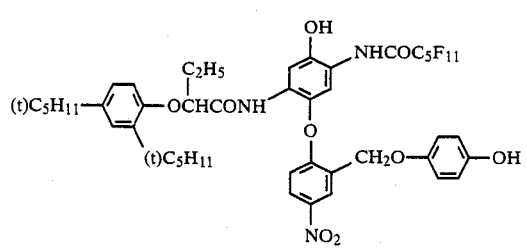 (9)
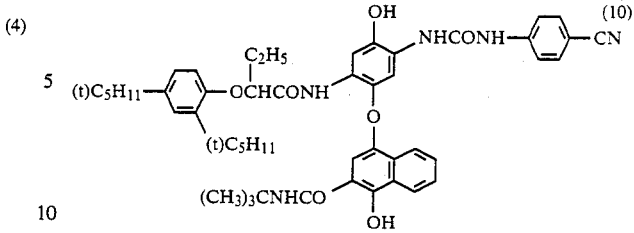 (10)
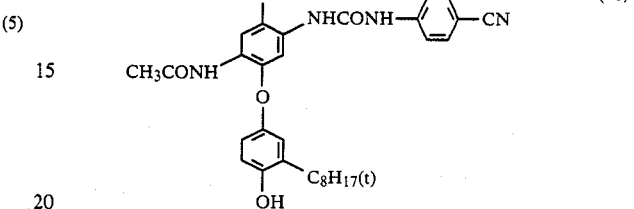 (11)
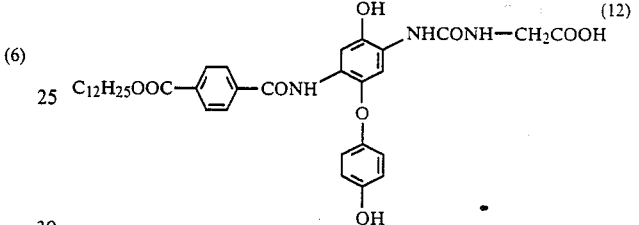 (12)
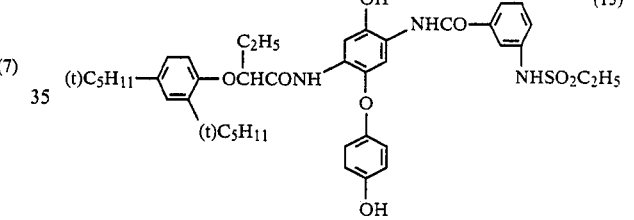 (13)
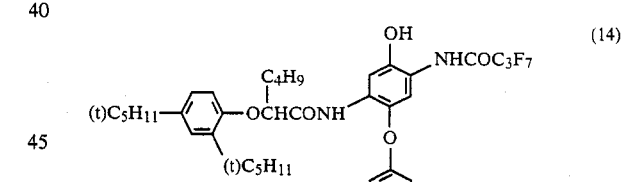 (14)
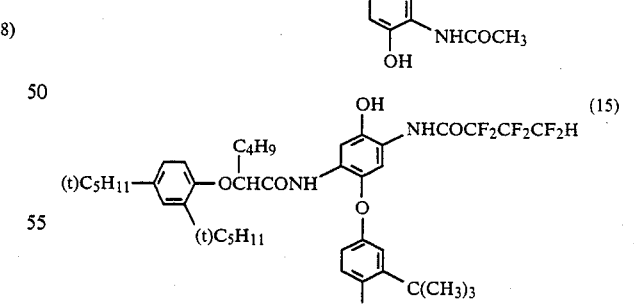 (15)
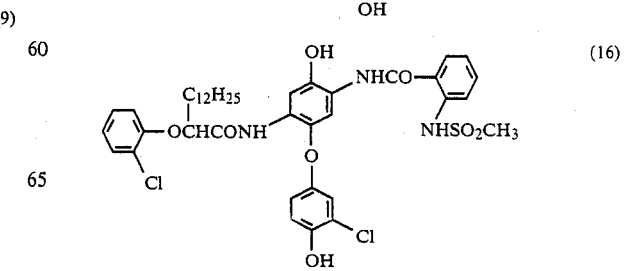 (16)

-continued
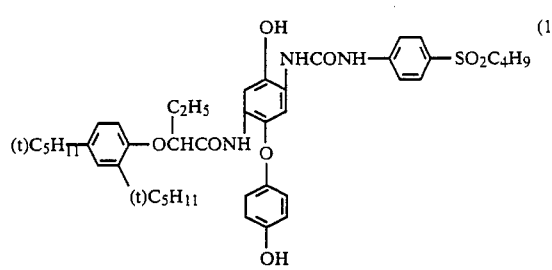
(17)
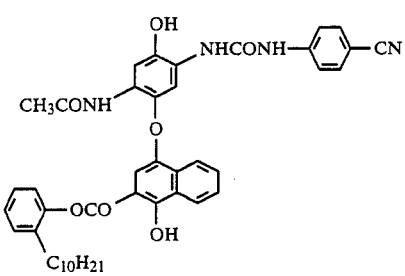
(18)
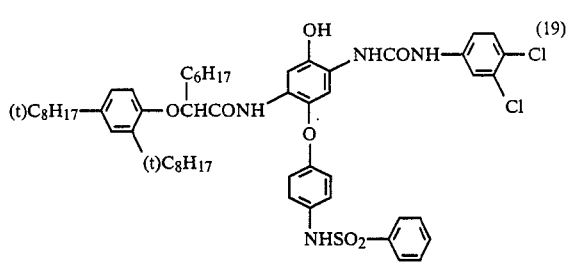
(19)
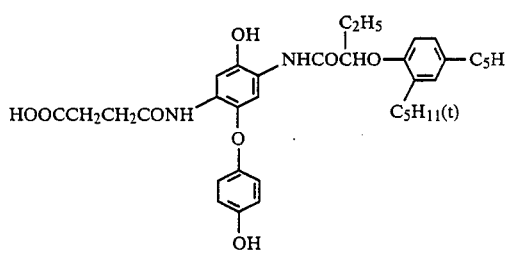
(20)
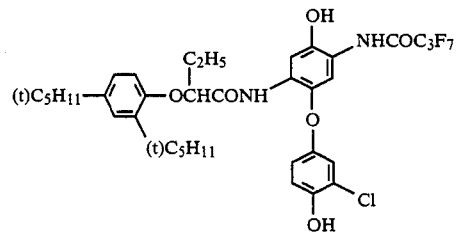
(21)
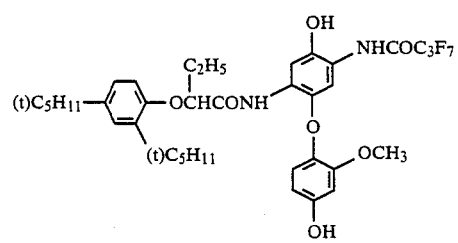
(22)
-continued
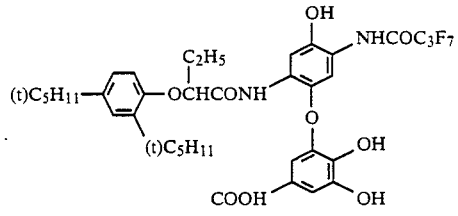
(23)
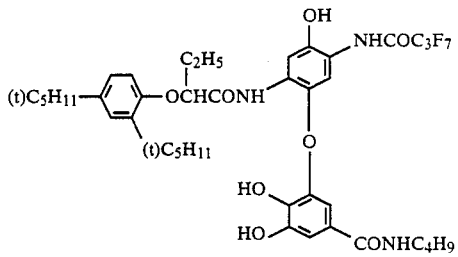
(24)
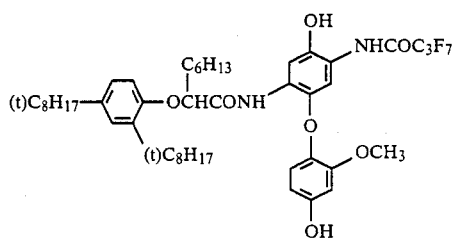
(25)
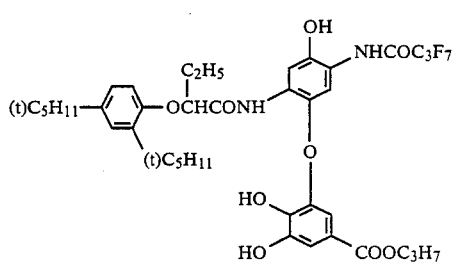
(26)
Examples of cyan couplers represented by formula (III)
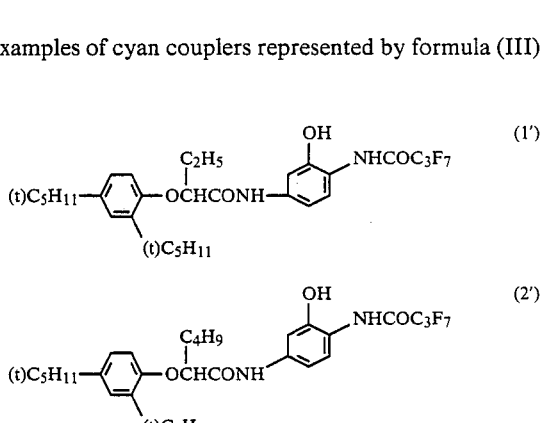
(1')
(2')
(3')

-continued
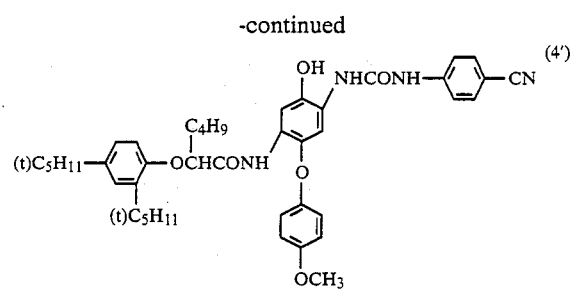
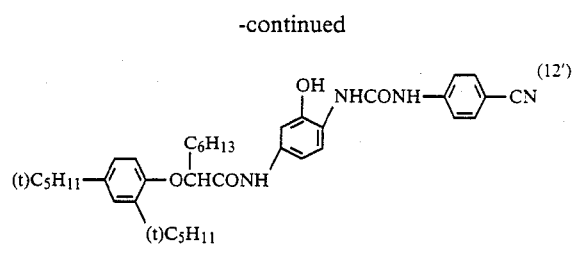
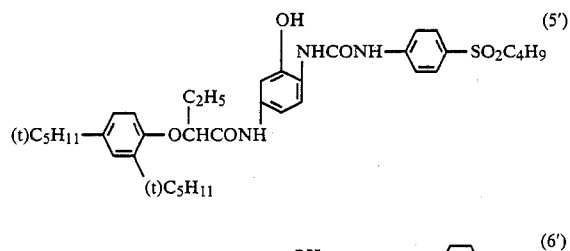
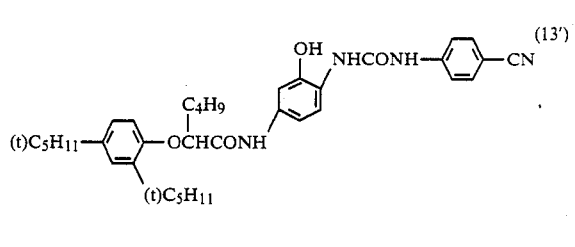
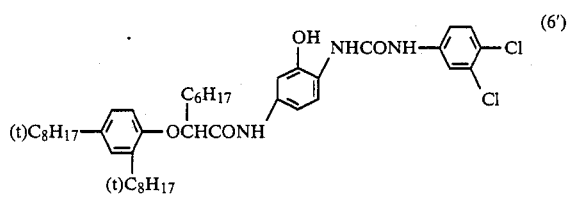
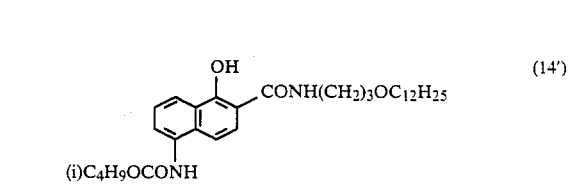
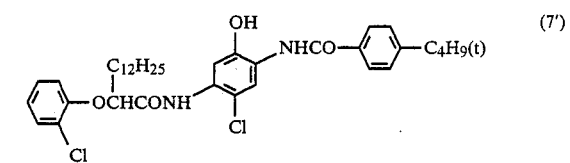
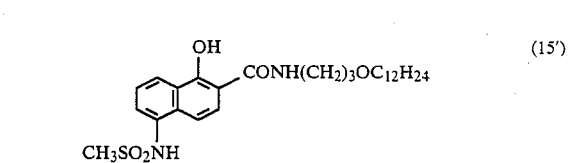
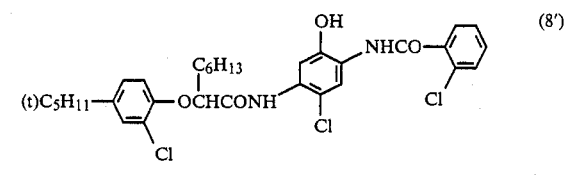
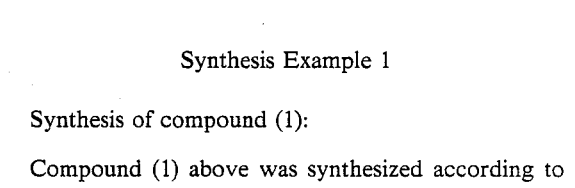
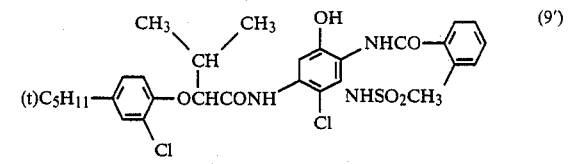
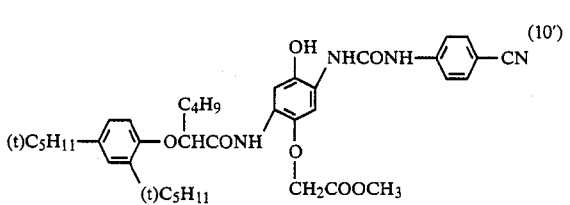
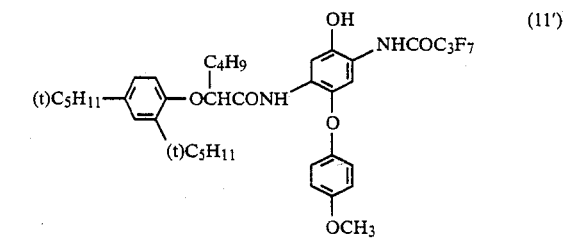
Synthesis Example 1
Synthesis of compound (1):
Compound (1) above was synthesized according to the following reaction scheme and description thereof.
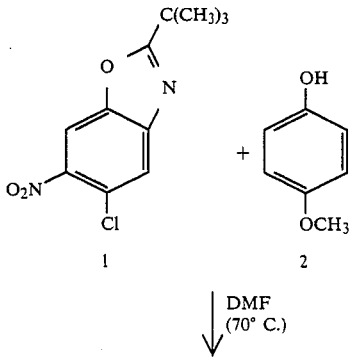

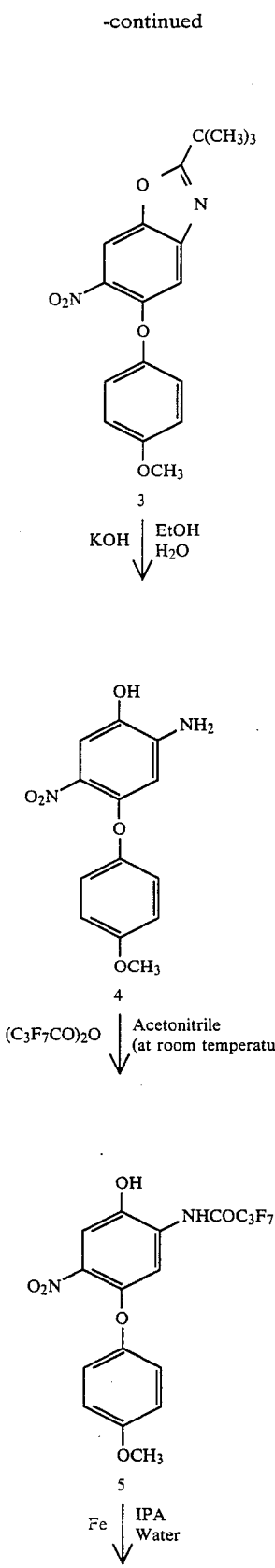
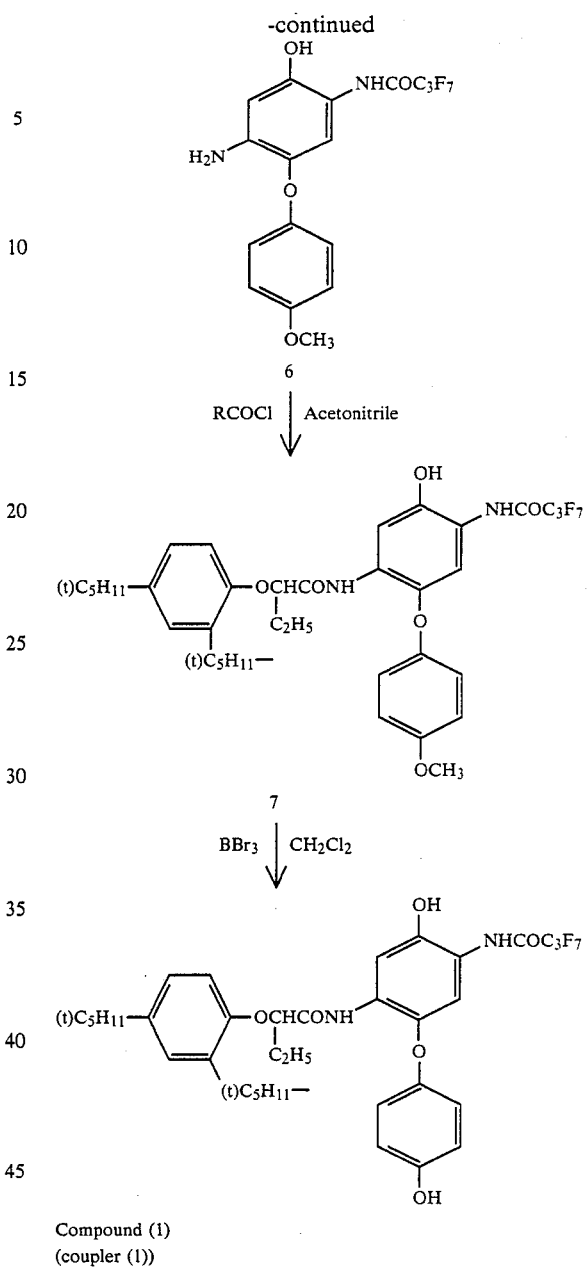

Compound (1)
(coupler (1))

Step (1): Synthesis of Compound 3

A mixture of 186 g of p-methoxyphenol and 99 g of potassium hydroxide was refluxed for 3 hours by using toluene as a solvent. After distilling away water and toluene, 275 g of Compound 1 and 500 ml of dimethylformamide were added to the thus formed residue and they were reacted for 3 hours at 70° C.

To the reaction mixture was gradually added 500 ml of methanol and the thus deposited crystals were separated by filtration to obtain 185 g of Compound 3.

Step (2): Synthesis of Compound 4

In a mixed solvent of 600 ml of ethanol and 200 ml of water was dissolved 185 g of Compound 3, and after adding thereto 135 g of potassium hydroxide, the mixture was refluxed for 3 hours. The thus obtained reaction mixture was neutralized with diluted hydrochloric acid and the thus deposited crystals were separated by filtration to obtain 136 g of Compound 4.

Step (3): Synthesis of Compound 5

A mixture of 136 g of Compound 4 and 1 liter of acetonitrile was added dropwise to 230 g of anhydrous perfluorobutanoic acid at room temperature (e.g., 20° to 25° C., hereinafter the same). After stirring the mixture for one hour, water was gradually added to the thus obtained reaction mixture and the thus deposited crystals were separated by filtration and recrystallized from a mixture of hexane and ethyl acetate to obtain 203 g of Compound 5.

Step (4): Synthesis of Compound 6

A mixture of 120 g of reduced iron, 7 g of ammonium chloride, 7 ml of acetic acid, 80 ml of water, and 600 ml of isopropyl alcohol (IPA) was refluxed for 5 minutes. To the mixture was gradually added 100 g of Compound 5 white refluxing. After 30 minutes, the thus obtained reaction miture was filtered off and the thus obtained filtrate was concentrated. The crude crystals obtained were recrystallized from a mixture of diethyl ether and hexane to obtain 84 g of Compound 6.

Step (5): Synthesis of Compound 7

In 500 ml of acetonitrile was dissolved 84 g of Compound 6 and then 64 g of carbonic acid chloride which became a ballast was added dropwise to the solution while refluxing. After continuing the reflux for 30 minutes, the thus obtained reaction mixture was ice-cooled and the thus deposited crystals were separated by filtration to obtain 118 g of Compound 7.

Step (6): Synthesis of Compound (1) illustrated above:

In 800 ml of dichloromethane was dissolved 50 g of Compound 7 and the solution was cooled to 0° C. Then, 50.5 g of boron tribromide was added dropwise to the solution while maintaining the system at 0° C. After further stirring the mixture for 2 hours, water was gradually added dropwise to the thus obtained reaction mixture and the thus deposited crystals were separated by filtration. The crystals were treated with activated carbon and decolorized, and thereafter were recrystallized from a mixture of diethyl ether and hexane to obtain 25.4 g of Compound (1) having a melting point of 202.5° C. to 204.0° C.

Synthesis Example 2

Synthesis of Compound (2):

By following the same procedure as in Synthesis Example 1, except that 3-t-butyl-p-methoxyphenol was used in place of p-methoxyphenol in Step (1) of Synthesis Example 1 described above, Compound (2) was obtained. The melting point of the product was 216° C. to 217° C.

Synthesis Example 3

Synthesis of Compound (3):

By following the same procedure as in Synthesis Example 1, except that 3,4-dichlorophenyl isocyanate was used in place of anhydrous perfluorobutanic acid in Step (3) of Synthesis Example 1 and 2(2,4-di-t-amylphenoxy)hexanoyl chloride was used in place of carbonic acid chloride in Step (5), Compound (3) was obtained. The melting point of the product was 173° C. to 175° C.

Synthesis Example 4

Synthesis of Compound (4):

By following the same procedure as in Synthesis Example 1, except that 3-acetamido-4-methoxyphenol was used in place of p-methoxyphenol in Step (1) of Synthesis Example 1 and anhydrous perfluorobutanic acid was used in an amount of twice the amount of therein in Step (3), Compound (4) was obtained. The melting point of the product was 223° C. to 225° C.

The couplers for use in this invention and other couplers which can be used together with the aforesaid couplers can be introduced into silver halide emulsion layers by the method described, for example, in U.S. Pat. No. 2,322,027. For example, the coupler(s) are dissolved in a high-boiling organic solvent such as a phthalic acid alkyl ester (e.g., dibutyl phthalate, dioctyl phthalate, etc.), a phosphoric acid ester (e.g., diphenyl phosphate, triphenyl phosphate, tricresyl phosphate dioctylbutyl phosphate, etc.), a citric acid ester (e.g., tributyl acetylcitrate, etc.), a benzoic acid ester (e.g., octyl benzoate, etc.), an alkylamide (e.g., diethyllaurylamide, etc.), a fatty acid ester (e.g., dibutoxyethyl succinate, diethyl azerate, etc.), a trimesic acid ester (e.g., tributyl trimerimesate, etc.), etc., or a low-boiling point organic acid having a boiling point of about 30° to 150° C., such as a lower alkyl acetate (e.g., ethyl acetate, butyl acetate, etc.), ethyl propionate, secondary butyl alcohol, methyl isobutyl ketone, $\beta$-ethoxyethyl acetate, methylcellosolve acetate, etc., and then dispersed in an aqueous solution of a hydrophilic colloid. The aforesaid high-boiling organic solvent may be used as a mixture thereof with the aforesaid low-boiling organic solvent.

Also, the dispersing method due to the polymer as described, for example, in Japanese Patent Publication No. 39,853/76 and U.S. Pat. No. 4,214,047 and 4,304,769 can be used.

When couplers have an acid group such as carboxylic acid and sulfonic acid, the couplers can be introduced into hydrophilic colloid as alkaline aqueous solution.

As the binders or protective colloids which can be used for silver halide emulsion layers and interlayers of the photographic light-sensitive materials of this invention, gelatin is advantageously used, but other hydrophilic colloids may also be used, alone or together with gelatin.

As gelatin for use in this invention, a lime-processed gelatin as well as an acid-processed gelatin can be used. Details of production processes for gelatin are described in Arthur Veis *The Macromolecular Chemistry of Gelatin*, Academic Press, 1964.

For the photographic emulsions layer of the photographic light-sensitive materials of this invention, silver bromide, silver iodobromide, silver iodochlorobromide, silver chlorobromide, or silver chloride may be used as the silver halide. The silver halide for use in this invention is preferably silver iodobromide containing less than 15 mole% silver iodide. Silver iodobromide containing from 2 mole% to 12 mole% silver iodide is particularly preferred in this invention.

There is no particular restriction on the mean grain size of silver halide grains (the grain size is shown by the diameter of the silver halide grain when the silver halide is spherical grains or grains similar to sphere or is shown by a mean value based on the project areas using the edge length thereof as the grain size when the silver halide is cubic grains) in the photographic emulsions, but the mean size of silver halide grains is preferably less than 3 microns.

The grain size distribution of the silver halide grain sizes may be broad or narrow.

The silver halide grains in the photographic emulsions may have a regular crystal form such as a cubic form or an octahedral form, or may have an irregular crystal form such as a spherical form or a tabular form. Or further, the grains may be a composite of such crystal forms. Furthermore, the silver halide grains for use in this invention may be composed of a mixture of silver halide grains having various crystal forms.

Also, a silver halide emulsion containing tabular silver halide grains having a diameter longer than 5 times the thickness thereof in about 50% of the whole project areas of the silver halide grains in the silver halide emulsion may be used in this invention.

The silver halide grains for use in this invention may have a different phase between the inside thereof and the surface layer thereof. Also, the silver halide grains may form latent images mainly on the surfaces thereof or ones forming latent images mainly in the inside thereof.

The silver halide emulsions for use in this invention can be prepared by the methods described, for example, in P. Glafkides, *Chimie et Physique Photographique,* (Paul Montel Co., pages 329 to 425, 1967; G. F. Duffin, *Photographic Emulsion Chemistry,* The Focal Press, pages 57 to 84, 1966; V. L. Zelikman et al, *Making and Coating Photographic Emulsion,* The Focal Press, pages 69 to 87, 1964), etc. That is, the photographic emulsions may be prepared by an acid process, a neutralization process, an ammonia process, etc. Also, as the manner of reacting a soluble silver salt and a soluble halogen salt, a single jet method, a double jet method, or a combination thereof may be used.

A so-called reverse mixing method for forming silver halide grains in the presence of an excessive amount of silver ions can also be used.

As one mode of the double jet method, a so-called controlled double jet method of preparing silver halide grains while maintaining the pAg in the liquid phase wherein the silver halide grains are formed at a constant value can be used. According to this method, a silver halide emulsion containing silver halide grains having regular crystal sizes and almost uniform grain sizes can be obtained.

Two or more silver halide emulsions separately prepared can be used as a mixture thereof.

The silver halide grains may be formed or physically ripened in the presence of cadmium salt, a zinc salt, a lead salt, a thallium salt, an iridium salt or a complex salt thereof, a rhodium salt or a complex salt thereof, an iron salt or a complex salt thereof, etc.

The silver halide emulsions for use in this invention are usually chemically sensitized. The chemical sensitization can be performed using the methods described, for example, in H. Frieser, editor, *Die Grundlagen der Photographischen Prozesse mit Silverhalogeniden,* Akademische Verlagesgesellschaft, 1968, pages 675–734.

More particularly, such methods include a sulfur sensitization method using active gelatin or a sulfur-containing compound capable of reacting with silver (e.g., thiosulfates, thioureas, mercapto compounds, rhodanines, etc.); a reduction sensitization method using a reducing material (e.g., stannous salts, amines, hydrazine derivatives, formamidine sulfinic acid, silane compounds, etc.); and a noble metal sensitization method using a noble metal compound (e.g., gold complex salts and complex salts of metals belonging to group VIII of the periodic table, such as Pt, Ir, Pd, etc.). They can be used singly, or as a combination thereof.

The silver halide photographic emulsions or use in this invention may further contain various compounds for preventing the occurrence of fog during the production, storage, or photographic processing of the photographic light-sensitive materials of this invention, or for stabilizing the photographic properties of the photographic light-sensitive materials. Examples of these compounds include azoles such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (in particular, 1-phenyl-5-mercaptotetrazole), etc.; mercaptopyrimidines, mercaptotriazines, thioketo compounds such as oxazolinethione; azaindenes such as triazaindenes, tetraazaindenes (in particular, 4-hydroxy-substituted (1,3,3a,7)tetraazaindenes), pentaazaindenes, etc.; benzenethiosulfonic acid; benzenesulfinic acid; benzenesulfonic acid amide, etc.

The photographic light-sensitive materials of this invention may contain coating aid and various surface active agents in the photographic emulsion layers or other hydrophilic colloid layers for the purpose of antistatic property, improvement of sliding property, improvement of dispersibility, improvement of antisticking property, and improvement of photographic properties (e.g., accelerating development, increasing contrast, increasing sensitivity, etc.).

The silver halide photographic emulsion layers of the photographic light-sensitive materials of this invention may further contain polyalkylene oxide or the derivatives thereof, such as the ethers, esters, amines, etc., thioether compounds, thiomorpholines, quaternary ammonium compounds, urethane derivatives, urea derivatives, imidazole derivatives, 3-pyrazolidones, etc., for the purpose of increasing sensitivity, increasing contrast, or accelerating development.

The photographic light-sensitive materials of this invention can further contain dispersions of water-insoluble or water sparingly soluble synthetic polymers for improving the dimensional stability of the photographic emulsion layers and other synthetic colloid layers. Examples of the polymer are the polymers of an alkyl (meth)acrylate, an alkoxyalkyl (meth)acrylate, glycidyl (meth)acrylate, (meth)acrylamide, a vinyl ester (e.g., vinyl acetate), acrylonitrile, olefin, styrene, etc., singly or as a combination thereof, or further a combination of the aforesaid monomer and acrylic acid, methacrylic acid, $\alpha,\beta$-unsaturated dicarboxylic acid, hydroxyalkyl (meth)acrylate, sulfoalkyl (meth)acrylate, styrenesulfonic acid, etc.

The silver halide emulsions for use in this invention may be spectral-sensitized by methine dyes, etc. The dyes which are used for the purpose include cyanine dyes, merocyanine dyes, complex cyanine dyes, complex merocyanine dyes, holopolar cyanine dyes, hemicyanine dyes, styryl dyes, and hemioxonole dyes. Particularly useful dyes are cyanine dyes, merocyanine dyes, and complex merocyanine dyes. For these dyes, nuclei that can be applied are those usually utilized for cyanine dyes as basic heterocyclic nuclei.

Such nuclei include pyrroline nuclei, oxazoline nuclei, thiazoline nuclei, pyrrole nuclei, oxazole nuclei, thiazole nuclei, selenazole nuclei, imidazole nuclei, tetrazole nuclei, pyridine nuclei, etc.; nuclei formed by condensing aliphatic hydrocarbon rings to these nuclei; and nuclei formed by condensing aromatic hydrocarbon rings to these nuclei, such as indolenine nuclei, benzindolenine nuclei, indole nuclei, benzoxazole nuclei, naphthoxazole nuclei, benzothiazole nuclei, naphthothiazole nuclei, benzoselenazole nuclei, benzimidazole nuclei, quinoline nuclei, etc. These nuclei may be substituted on carbon atoms.

For the merocyanine dyes or complex merocyanine dyes, 5- or 6-membered heterocyclic nuclei can be applied, such as pyrazolin-5-one nuclei, thiohydantoin nuclei, 2-thiooxazolidine-2,4-dione nuclei, thiazolidine-2,4-dione nuclei, rhodanine nuclei, thiobarbituric acid nuclei, etc.

These sensitizing dyes may be used singly or as a combination thereof. A combination of sensitizing dyes is frequently used for the purpose of supersensitization.

The photographic emulsions may further contain a dye having no spectral sensitizing action by itself, or a material which does not substantially absorb visible light, but which shows a supersensitizing action together with a sensitizing dye. For example, the emulsions may contain aminostyryl compounds substituted by a nitrogen-containing heterocyclic group, as described, for example, in U.S. Pat. Nos. 2,933,390 and 3,635,721, aromatic organic acid-formaldehyde condensation products, as described, for example, in U.S. Pat. No. 3,743,510, cadmium salts, azaindene compounds, etc.

This invention can be applied to a multilayer multicolor photographic light-sensitive material having at least two photographic emulsion layers each having a different spectral sensitivity on a support. The multilayer multicolor photographic light-sensitive material usually has on a support at least one red-sensitive emulsion layer, at least one green-sensitive emulsion layer, and at least one blue-sensitive emulsion layer. The disposed order of these layer may be optionally selected according to the purposes. Usually, for multicolor reproduction the red-sensitive emulsion layer contains a cyan-forming coupler, a green-sensitive emulsion layer, a magenta-forming coupler, and a blue-sensitive emulsion layer a yellow-forming coupler, but other combination may be used as the case may be.

The photographic light-sensitive materials of this invention may further contain other dye-forming couplers in the photographic emulsion layers or light-sensitive layers, that is, compounds capable of coloring by the oxidative coupling with an aromatic primary amine developing agent (e.g., a phenylenediamine derivative, an aminophenol derivative, etc.) in color development processing together with the couplers shown by formulae (I) and (III). Examples of these dye-forming couplers include magenta couplers such as 5-pyrazolone couplers, pyrazolonbenzimidazole couplers, pyrazolotriazole couplers, pyrazoloimidazole couplers, pyrazolopyrazole couplers, pyrazolotriazole couplers, pyrazolotetrazole couplers, cyanoacetylcumarone couplers, open-chain acrylacetonitrile couplers, etc.; yellow couplers such as acylacetamide couplers (e.g., benzoylacetanilides, pivaloylacetanilides, etc.); and cyan couplers such as naphthol couplers and phenol couplers.

These couplers are preferably non-diffusible couplers having a hydrophobic group called as ballast group in the molecule or a polymerized coupler. The coupler may be four-equivalent or two-equivalent with respect to silver ion. Also, colored couplers having a color correction effect or so-called DIR (development inhibitor releasing) couplers capable of releasing a development inhibitor with development can be also used.

Also, the photographic light-sensitive materials of this invention may further contain a non-coloring DIR coupling compound which forms a colorless coupling reaction product and releases a development inhibitor. Also, the photographic light-sensitive material may contain a compound capable of releasing a development inhibitor with the progress of development in addition of DIR couplers.

Two or more kinds of the couplers for use in this invention represented by formula (I) and the above-described couplers (e.g., the couplers represented by formula (III) and others dye-forming couplers) may be used for the same emulsion layer for satisfying the characteristics required for the photographic light-sensitive layer or the same couplers may exist each in two or more layers.

The photographic light-sensitive materials of this invention may further contain inorganic or organic hardening agents in the photographic emulsion layers or in other hydrophilic colloid layers. Examples of such hardening agents include chromium salts (chromium alum, chromium acetate, etc.), aldehydes (e.g., formaldehyde, glyoxal, glutaraldehyde, etc.), N-methylol compounds (e.g., dimethylolurea, methyloldimethylhydantoin, etc.), dioxane derivatives (e.g., 2,3-dihydroxydioxane, etc.), active vinyl compounds (e.g., 1,3,5-triacryloyl-hexahydro-s-triazine, 1,3-vinylsulfonyl-2-propanol, etc.), active halogen compounds (e.g., 2,4-dichloro-6-hydroxy-s-triazine, etc.), mucohalogenic acids (e.g., mucochloric acid, mucophenoxychloric acid, etc.), etc. They can be used singly or as a combination thereof.

When the photographic light-sensitive materials of this invention contain dyestuff or ultraviolet absorbents in hydrophilic colloid layers, the dyestuff or ultraviolet absorbents may be mordanted by polymers such as a cationic polymer, etc.

Also, the photographic light-sensitive materials of this invention may further contain hydroquinone derivatives, aminophenol derivatives, gallic acid derivatives, ascorbic acid derivatives, etc. as anticolor foggants.

The photographic light-sensitive materials of this invention may further contain ultraviolet absorbents in the hydrophilic colloid layers. Examples of such ultraviolet absorbents include benzotriazole compounds substituted by aryl group, as described, for example, in U.S. Pat. No. 3,533,794; 4-thiazolidone compounds, as described, for example, in U.S. Pat. Nos. 3,314,794 and 3,352,681; benzophenone compounds, as described, for example, in U.S. Pat. No. 3,785,827; cinnamic acid ester compounds, as described, for example, in U.S. Pat. Nos. 3,705,805 and 3,707,375; butadiene compounds, as described, for example, in U.S. Pat. No. 4,045,229; and benzoxazole compounds, as described, for example, in U.S. Pat. No. 3,700,455. In this invention, ultraviolet absorptive couplers (e.g., α-naphtholic cyan dye-forming couplers) or ultraviolet absorptive polymers may be used. These ultraviolet absorbents may be mordanted to specific layers.

The photographic light-sensitive materials of this invention may further contain water-soluble dyestuff in the hydrophilic colloid layers as filter dyes or for anti-irradiation and other various purposes. Examples of such dyestuff are oxonol dyestuff, hemioxonol dyestuff, styryl dyestuff, merocyanine dyestuff, cyanine dyestuff, and azo dyestuff. Of these dyes, oxonol dyestuff, hemioxonol dyestuff, and merocyanine dyestuff are most advantageous.

At the practice of this invention, known anti-fading agents or image stabilizers may be used together with the above-described couplers. The dye image stabilizers may be used singly or as a mixture thereof. Examples of the anti-fading agents are hydroquinone derivatives, gallic acid derivatives, p-alkoxyphenols, p-oxyphenol derivatives, and bisphenols.

For photographic processing the color photographic light-sensitive materials of this invention, known processes and processing liquids described in *Research Disclosure*, RD No. 176, pages 28–30 (December, 1978) can be used. It is preferred that the processing temperature is from 18° C. to 50° C., but the temperature may be lower than 18° C. or higher than 50° C., if desired.

The color developer which is used for processing the photographic light-sensitive materials of this invention is composed of an alkaline aqueous solution containing a color developing agent. The color developing agent for use in this invention includes known primary aromatic amine developing agents such as phenylenediamines (e.g., 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfoamidoethylaniline, 4-amino-3-methyl-N-ethyl-N-$\beta$-methoxyethylaniline, etc.).

Other color developing agents described in L. F. A. Mason, *Photographic Processing Chemistry*, (The Focal Press, 1966, pages 226–229, U.S. Pat. Nos. 2,193,015, 2,592,364, and 3,816,134, etc. can be used in this invention.)

The color developer may further contain a pH buffer such as the sulfite, carbonate, borate or phosphate of an alkali metal and a development inhibitor or an anti-foggant such as a bromide, iodide, and organic antifoggants. Also, if desired, the color developer may further contain a hard water softening agent, a preservative such as hydroxylamine, an organic solvent such as benzylalcohol, diethylene glycol, etc., a development accelerator such as polyethylene glycol, a quaternary ammonium salt, amines, etc., dye-forming couplers, competing couplers, a fogging agent such as sodium boron hydroxide, an auxiliary developing agent such as 1-phenyl-3-pyrazolidone, tackifier, a polycarboxylic acid series chelating agent, an antioxidant, etc.

The color photographic light-sensitive materials of this invention are usually bleached after color development. The bleaching process may be performed simultaneously with or separately from a fixing process. Examples of the bleaching agent are compounds of a multivalent metal such as iron(III), cobalt(III), chromium(VI), copper(II), etc., peracids, quinones, nitroso compounds, etc. Examples include ferrycianides, dichloromates, organic complex salts of iron(III) or cobalt(III), aminopolycarboxylic acids (e.g., ethylenediaminetetraacetic acid, nitrilotriacetic acid, 1,3-diamino-2-propanoltetraacetic acid, etc.), complex salts of organic acids (e.g., citric acid, tartaric acid, malic acid, etc.), persulfates, permanganates, nitrosophenol, etc. In these compounds, potassium ferricyanide, sodium ethylenediaminetetraacetato ferrate(III) and ammonium ethylenediaminetetraacetato ferrate(III) are particularly useful. Ethylenediaminetetraacetic ferrate(III) complex salts are advantageous for both the bleaching solution and the mono bath blixing solution.

The fixing solution may use a conventional composition. The fixing agent includes a thiosulfate, a thiocyanate, and organic sulfur compounds which are known to have an effect as a fixing agent. The fixing solution may contain a water-soluble aluminum salt as a hardening agent.

Hereafter this invention will be described in more detail reference to the following examples, although this invention is not limited thereto. All parcents are by weight unless otherwise indicated.

EXAMPLE 1

In a mixture of 100 ml of tricresyl phosphate and 100 ml of ethyl acetate was dissolved 100 g of a cyan coupler, 2-(heptafluorobutylamido)-5-{2'-)2'',4''-di-tert-amylphenoxy)butylamido}phenol (Coupler (1')). To the solution were added 10 g of sodium dodecylbenzenesulfonate and 1 kg of an aqueous 10 wt% gelatin solution, and the mixture was stirred at high speed to obtain an emulsion.

After dispersing 1 kg of the emulsion in 1 kg of a red-sensitive iodobromide emulsion (iodine content: 3 mole%, silver content: 70 g, gelatin content: 60 g, mean grain size: 0.7 $\mu$m), the mixture was coated on a triacetate base at a dry thickness of 2.5 $\mu$m (silver content coated: 0.8 g/m$^2$) and dried to obtain Sample 1.

Also, by following the same procedure as above, using about 50 g of Coupler (1') described above and about 50 g of each of the compounds (couplers) for use in this invention represented by formula (I) as indicated in Table 1, each of the emulsions was prepared to obtain Samples 2 to 8 and 10.

Further, as Comparative Example, the emulsion of sample 9 was prepared by following the same procedure as above except that comparative coupler (1) was used in place of the coupler represented by formula (I). By using these emulsions, the samples in Table 1 were prepared by following the above procedure. Comparative Compound (1)

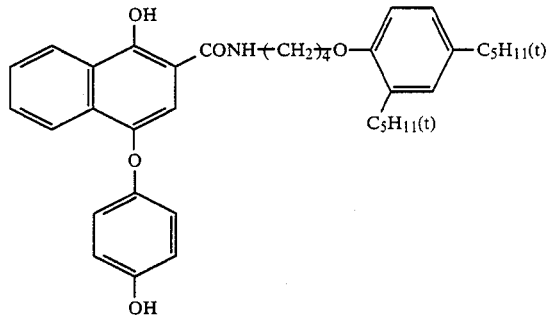

TABLE 1

| Sample No. | Main Coupler | | Addition Coupler | |
|---|---|---|---|---|
| 1 | Coupler (1') 100 g | | | |
| 2 | Coupler (1') 50 g | + | Coupler | (1) 60 g |
| 3 | Coupler (1') 50 g | + | Coupler | (2) 63 g |
| 4 | Coupler (1') 50 g | + | Coupler | (3) 59 g |
| 5 | Coupler (1') 50 g | + | Coupler | (4) 76 g |
| 6 | Coupler (1') 50 g | + | Coupler | (5) 66 g |
| 7 | Coupler (1') 50 g | + | Coupler | (6) 60 g |
| 8 | Coupler (1') 50 g | + | Coupler | (7) 71 g |
| 9 | Coupler (1') 50 g | + | Comparative Compound | (1) 47 g |
| 10 | Coupler (3') 65 g | + | Coupler | (1) 60 g |

Sample 1: Control sample;
Samples 2 to 8 and 10: Samples of this invention;
Sample 9: Comparative Each of Samples 1 to 10 was light-exposed and subjected to color reversal processing to form color images. The color images were allowed to stand under conditions of 80° C. and 60% relative humidity for 30 days, and then the reduction in color density was measured for each sample.

Residual Percentage (%) =

$$\frac{\text{Density after preservation}}{\text{Initial density}} \times 100\ (\%)$$

The results obtained are shown in Table 2 below.

TABLE 2

| Sample No. | Initial Density | Density After Preservation | Fastness (Residual Percentage) |
|---|---|---|---|
| 1 (Control) | 3.0 | 2.7 | 90% |
| 2 (Invention) | 2.2 | 2.1 | 95% |
| 3 (Invention) | 2.1 | 1.9 | 90% |
| 4 (Invention) | 2.2 | 2.0 | 91% |
| 5 (Invention) | 2.3 | 2.1 | 91% |
| 6 (Invention) | 2.2 | 2.1 | 95% |
| 7 (Invention) | 2.1 | 1.9 | 90% |
| 8 (Invention) | 2.2 | 2.0 | 91% |
| 9 (Comparison) | 2.3 | 1.8 | 78% |
| 10 (Invention) | 2.3 | 2.1 | 91% |

From the results shown above, it can be seen that the dye residual percentage (i.e., fastness) of Samples 2 to 8 using the couplers for use in this invention is very excellent, particularly as compared to Sample 9 using a comparative coupler.

Furthermore, each of Samples 1 to 10 was exposed through an optical wedge for measuring graininess and after being subjected to color reversal processing, the RMS graininess of each image thus formed was measured by the density measurement using a microdensitometer. The graininess at image densities of 1.0 and 2.0 thus obtained are shown in Table 3 below.

TABLE 3

| Sample No. | RMS Graininess | |
|---|---|---|
| | Density 1.0 | Density 2.0 |
| 1 (Control) | 23 | 30 |
| 2 (Invention) | 16 | 22 |
| 3 (Invention) | 15 | 21 |
| 4 (Invention) | 17 | 24 |
| 5 (Invention) | 17 | 25 |
| 6 (Invention) | 16 | 22 |
| 7 (Invention) | 15 | 20 |
| 8 (Invention) | 17 | 23 |
| 9 (Comparison) | 18 | 26 |
| 10 (Invention) | 17 | 25 |

From the results shown above, it can be seen that the graininess of Samples 2 to 8 and 10 of this invention using a mixture of the conventional coupler and each of the couplers of this invention is greatly improved as compared with Control Sample 1 using the conventional coupler only. The graininess in Comparative Sample 9 is also improved to some extent, but, as was noted above, the self life (i.e., fastness) of the color images is reduced.

EXAMPLE 2

Sample 11 was prepared by coating the following emulsion layers and auxiliary layers shown below, in succession, on a triacetyl cellulose support having a subbing layer.

Layer 1: Slow-speed red-sensitive emulsion layer:

In a mixture of 100 ml of tricresyl phosphate and 100 ml of ethyl acetate was dissolved 100 g of a cyan coupler, 2-(heptafluorobutylamido)-5-2'-(2'',4''-di-t-amylphenoxy)butylamido phenol and after adding thereto 1 kg of an aqueous 10 wt% gelatin solution and 10 g of a surface active agent, sodium dodecylbenzenesulfonate, the mixture was stirred at high speed to obtain an emulsion. Then, 500 g of the emulsion was added to 1 kg of a slow-speed red-sensitive silver iodobromide emulsion (mean grain size of silver halide grains: 0.3 μm, silver content: 70 g, gelatin content: 60 g, iodine content: 3 mole%) together with gelatin, water, a stabilizer, a coating aid, etc., and the thus obtained mixture was coated on the support at a dry thickness of 2 μm (silver content coated: 0.6 g/m$^2$).

Layer 2: Medium-speed red-sensitive emulsion layer:

After mixing 1 kg of the emulsion of the cyan coupler as used for Layer 1 with 1 kg of a medium-speed red-sensitive silver iodobromide emulsion (mean grain size of silver halide grains: 0.5 μm, silver content: 70 g, gelatin content: 60 g, iodine content: 3 mole%) together with gelatin, water, a stabilizer, a coating aid, etc., the thus obtained mixture was coated on Layer 1 at a dry thickness of 1 μm (silver content: 0.4 g/m$^2$).

Layer 3: High-speed red-sensitive emulsion layer:

After mixing 1 kg of the emulsion of the cyan coupler as used for layer 1 with/kg a high-speed red-sensitive silver iodobromide emulsion (mean grain size of silver halide grains: 0.6 μm, silver content: 70 g, gelatin content: 60 g, iodine content: 3 mole%) together with gelatin, water, a stabilizer, a coating aid, etc., the thus obtained mixture was coated on Layer 2 at a dry thickness of 1 μm (silver content: 0.4 g/m$^2$).

Layer 4: Interlayer:

In 200 ml of ethyl acetate was dissolved 200 g of 2,5-di-sec-octylhydroquinone and after adding thereto 1 kg of an aqueous 10 wt% gelatin solution and 20 g of a surface active agent, sodium dodecylbenzenesulfonate, the thus obtained mixture was stirred at high-speed to obtain an emulsion. The thus obtained emulsion was mixed with gelatin, water, a coating aid, etc., and the resultant mixture was coated on Layer 3 at a dry thickness of 1 μm.

Layer 5: Slow speed green-sensitive emulsion layer:

By following the same procedure as the case of preparing the emulsion for Layer 1 except that a magenta coupler, 1-(2,4,6-trichlorophenyl)-3-{3-(2,4-di-t-amylphenoxyacetamido)benzamido}-5-pyrazolone was used as the coupler, an emulsion was prepared. After mixing 500 g of the emulsion with 1 kg of a green-sensitive low-speed silver iodobromide emulsion (mean grain size: 0.3 μm, silver content: 70 g, gelatin content: 60 g, iodine content: 3 mole%), together with gelatin, water, a stabilizer, a coating aid, etc., the thus obtained mixture was coated on Layer 4 at a dry thickness of 2 μm (silver content: 0.7 g/m$^2$).

Layer 6: Medium-speed green-sensitive emulsion layer:

After mixing 1 kg of the emulsion of the magenta coupler for Layer 5 with 1 kg of a medium-speed green-sensitive silver iodobromide emulsion (mean grain size: 0.5 μm, silver content: 70 g of silver, gelatin content: 60 g, iodine content: 3 mole%) together with gelatin, water, a stabilizer, a coating aid, etc., the thus obtained mixture was coated on Layer 5 at a dry thickness of 1 μm (silver content: 0.4 g/m$^2$).

Layer 7: High-speed green-sensitive emulsion layer:

After mixing 1 kg of the emulsion of the magenta coupler as used for Layer 5 with 1 kg of a green-sensitive high-speed slver iodobromide emulsion (mean grain size: 0.7 μm, silver content: 70 g, gelatin content: 60 g, iodine content: 3 mole%) together with gelatin, water, a stabilizer, a coating aid, etc., the thus mixture obtained was coated on Layer 6 at a dry thickness of 1 μm (silver content: 0.4 g/m$^2$).

Layer 8: Interlayer:

After mixing 1 kg of the emulsion as used for Layer 4 with gelatin, water, a coating aid, etc., the resultant mixture was coated on Layer 7 at a dry thickness of 0.5 μm.

Layer 9: Yellow filter layer:

A mixture of yellow colloid silver and gelatin was coated on Layer 8 at a dry thickness of 1 μm.

Layer 10: Slow-speed blue-sensitive emulsion layer:

By following the same procedure as the case of preparing Layer 1 except that a yellow coupler, α-(pivaloyl)-α-(1-benzyl-5-ethoxy-3-hydantoinyl)-2-chloro-5-dodecyloxycarbonylacetanilide in place of the cyan coupler as used for Layer 1 was used and the amounts of tricresyl phosphate and ethyl acetate were changed to 120 ml and 120 ml, respectively, an emulsion was prepared. Then, 1 kg of the emulsion was mixed with 1 kg of a slow-speed blue-sensitive silver iodobromide emulsion (mean grain size: 0.5 μm, silver content: 70 g, gelatin content: 60 g, iodine content: 3 mole%) together with gelatin, water, a stabilizer, a coating aid, etc., the mixture was coated on Layer 9 at a dry thickness of 2 μm (silver content: 0.6 g/m$^2$).

Layer 11: Medium-speed blue-sensitive emulsion layer:

After mixing 1 kg of the emulsion of the yellow coupler as used for Layer 10 with 1 kg of a medium speed blue-sensitive silver iodobromide emulsion (mean grain size: 0.6 μm, silver content: 70 g, gelatin content: 60 g, iodine content: 3 mole%) together with gelatin, water, a stabilizer, a coating aid, etc., the mixture was coated on Layer 10 at a dry thickness of 1 μm (silver content: 0.4 g/m$^2$).

Layer 12: High-speed blue-sensitive emulsion layer:

After mixing 1 kg of the emulsion of the yellow coupler as used for Layer 12 with 1 kg of a high-speed blue-sensitive silver iodobromide emulsion (mean grain size: 0.7 μm, silver content: 70 g, gelatin content: 60 g, iodine content: 3 mole%) together with gelatin, water, a stabilizer, a coating aid, etc., the thus obtained mixture was coated on Layer 11 at a dry thickness of 1 μm (silver content: 0.4 g/m$^2$).

Layer 13: Second protective layer:

In a mixture of 200 ml of tricresyl phosphate and 200 ml of ethyl acetate were dissolved 15 g of 5-chloro-2-(2-hydroxy-3,5-di-t-butylphenyl)-2H-benzotriazole, 30 g of 2-(2-hydroxy-5-t-butylphenyl)-2H-benzotriazole, 35 g of 2-(2-hydroxy-3-sec-butyl-5-t-butylphenyl)-2H-benzotriazole, and 100 g of dodecyl-5-(N,N-diethylamino)-2-benzenesulfonyl-2,4-pentadienoate as ultraviolet absorbents in place of a coupler and after adding thereto 20 g of sodium dodecylbenzenesulfonate and 2 kg of an aqueous 10 wt% gelatin solution, the mixture was stirred at high speed to obtain an emulsion. Then, 1 kg of the emulsion was mixed with gelatin, water, a coating aid, etc., the resultant mixture was coated on Layer 12 at dry thickness of 2 μm (a coating amount of all ultraviolet absorbents: 0.5 g/m$^2$).

Layer 14: First protective layer:

After mixing a fine grain silver iodobromide emulsion (mean grain size: 0.1 μm, silver content: 70 g, gelatin content: 60 g, iodine content: 1 mole%) which was not chemically sensitized with gelatin, water, a stabilizer, a coating aid, the mixture was coated on Layer 13 at a dry thickness of 1 μm (silver content: 0.3 g/m$^2$).

Thus, a multilayer color photographic film (Sample 11) was obtained.

Then, Samples 12 to 20 were also prepared by following the same procedure as above except that 1 kg of each of emulsions for Samples 2 to 10 as used in Example 1 was used in place of the emulsion of the cyan coupler used for Layers 1 to 3.

Each of the thus prepared samples was exposed, developed and allowed to stand under the same conditions as in Example 1, and then the residual percentage (fastness) of the color images thus formed was determined by measuring the cyan density through a red filter. Also, the graininess of the cyan dye images was measured through a red filter as RMS graininess as in Example 1.

The results thus obtained are shown in Table 4.

TABLE 4

| Sample. No. | Fastness (Residual percentage) | RMS Graininess | |
|---|---|---|---|
| | | Density 1.0 | Density 2.0 |
| 11 | 94% | 25 | 32 |
| 12 | 98% | 17 | 23 |
| 13 | 92% | 16 | 23 |
| 14 | 93% | 17 | 25 |
| 15 | 93% | 17 | 26 |
| 16 | 96% | 17 | 23 |
| 17 | 95% | 16 | 24 |
| 18 | 92% | 18 | 24 |
| 19 | 85% | 18 | 27 |
| 20 | 98% | 16 | 23 |

Sample 11: Control sample
Samples 12-18 and 20: Samples of this invention
Sample 19: Comparative sample.

From the results shown above, it can be seen that in multilayer samples, the samples of this invention using the cyan couplers of this invention have improved heat stability (fastness in dark-heat place) and improved graininess as compared with Sample 11 using a conventional coupler and Sample 19 using the comparative compound.

EXAMPLE 3

Sample 21 of a multilayered color light-sensitive material was prepared by coating the following layers having the composition shown below, in succession, on a transparent triacetyl cellulose support. Further, gelatin hardening agent H-1 and surface active agent other than the below-compositions were coated on each layer.

Layer 1: Antihalation layer
Black colloide silver: 0.15 g/m$^2$
U-1 (UV ray absorbent): 0.08 g/m$^2$
U-2 (UV ray absorbent): 0.12 g/m$^2$
Layer 2: Interlayer
2,5-di-tert-pentadecyl hydroquinone: 0.08 g/m$^2$
Coupler C-1: 0.11 g/m$^2$
Layer 3: First red-sensitive emulsion layer
Silver bromoiodide emulsion: 1.2 g/m$^2$ (mean grain size: 0.4 μm; silver iodide (AgI) content: 4 mol%)
Sensitizing dye I: $1.4 \times 10^{-4}$ mol/mol-Ag
Sensitizing dye II: $0.4 \times 10^{-4}$ mol/mol-Ag
Sensitizing dye III: $5.6 \times 10^{-4}$ mol/mol-Ag
Sensitizing dye IV: $4.0 \times 10^{-4}$ mol/mol-Ag
Coupler C-2: 0.52 g/m$^2$
Coupler C-3: 0.035 g/m$^2$
Coupler C-4: 0.025 g/m$^2$
Layer 4: Second red-sensitive emulsion layer Silver bromoiodide emulsion: 1.0 g/m$^2$ (mean grain size: 0.8 μm; silver iodide (AgI) content: 8 mol%)
Sensitizing dye I: $5.2 \times 10^{-5}$ mol/mol-Ag
Sensitizing dye II: $1.5 \times 10^{-5}$ mol/mol-Ag
Sensitizing dye III: $2.1 \times 10^{-4}$ mol/mol-Ag
Sensitizing dye IV: $1.5 \times 10^{-5}$ mol/mol-Ag
Coupler C-2: 0.055 g/m$^2$
Coupler C-5: 0.120 g/m$^2$
Coupler C-3: 0.035 g/m$^2$
Layer 5: Interlayer
2,5-di-tert-pentadecyl hydroquinone: 0.18 g/m$^2$
Layer 6: First green-sensitive emulsion layer
Silver bromoiodide emulsion: 0.80 g/m$^2$ (mean grain size: 0.4 μm; silver iodide (AgI) content: 4 mol%)
Sensitizing dye V: $4.0 \times 10^{-4}$ mol/mol-Ag
Sensitizing dye VI: $3.0 \times 10^{-5}$ mol/mol-Ag
Sensitizing dye VII: $1.0 \times 10^{-4}$ mol/mol-Ag
Coupler C-6: 0.45 g/m$^2$
Coupler C-7: 0.13 g/m$^2$
Coupler C-8: 0.02 g/m$^2$
Coupler C-4: 0.04 g/m$^2$
Layer 7: Second green-sensitive emulsion layer
Silver bromoiodide emulsion: 0.85 g/m$^2$ (mean grain size: 0.8 μm; silver iodide (AgI) content: 8 mol%)
Sensitizing dye V: $2.7 \times 10^{-4}$ mol/mol-Ag
Sensitizing dye VI: $1.8 \times 10^{-5}$ mol/mol-Ag
Sensitizing dye VII: $7.5 \times 10^{-5}$ mol/mol-Ag
Coupler C-6: 0.095 g/m$^2$
Coupler C-7: 0.015 g/m$^2$
Layer 8: Yellow filter layer
Yellow colloide silver: 0.08 g/m$^2$
2,5-di-tert-pentadecyl hydroquinone: 0.090 g/m$^2$
Layer 9: First blue-sensitive emulsion layer
Silver bromoiodide emulsion: 0.37 g/m$^2$ (mean grain size: 0.3 μm; silver iodide (AgI) content: 5 mol%)
Sensitizing dye VIII: $4.4 \times 10^{-4}$ mol/mol-Ag
Coupler C-9: 0.71 g/m$^2$
Coupler C-4: 0.07 g/m$^2$
Layer 10: Second blue-sensitive emulsion layer
Silver bromoiodide emulsion: 0.55 g/m$^2$ (mean grain size: 0.9 μm; silver iodide (AgI) content: 7 mol%)
Sensitizing dye VIII: $3.0 \times 10^{-4}$ mol/mol-Ag
Coupler C-9: 0.23 g/m$^2$
Layer 11: First protective layer
U-1 (UV ray absorbent): 0.14 g/m$^2$
U-2 (UV ray absorbent): 0.22 g/m$^2$
Layer 12: Second protective layer
Silver bromoiode emulsion: 0.25 g/m$^2$ (mean grain size: 0.07 μm; silver iodide (AgI) content: 2 mol%)
Polymethacrylate grain: 0.10 g/m$^2$ (diameter = 1.5 μm)

SAMPLES 22 TO 24

Samples 22 to 24 were prepared by the same procedure as the case of preparing Sample 21 except that the coupler of the present invention was used in an amount of 50 mol% in place of Coupler C-2 for Layer 9 of Sample 21.

These samples were subjected to imagewise exposure for sensitometry using a red filter, and then color development processing as described below. Further, these samples were exposed to light for a conventional measurement of RMS (aperture: 48 μm), and subjected to the same color development processing. As a result, the photographic and graininess properties of the thus obtained samples were determined by using a red filter.

The development processing was carried out at 38° C. according to the following processing steps.

| Processing Steps | Time |
|---|---|
| 1. Color development | 3 min and 15 sec |
| 2. Bleaching | 6 min and 30 sec |
| 3. Washing with water | 3 min and 15 sec |
| 4. Fixing | 4 min and 20 sec |
| 5. Washing with water | 3 min and 15 sec |
| 6. Stabilizing | 3 min and 15 sec |

The composition of each processing solution used in the above-described processing is as follows.

| Color Developing Solution | |
|---|---|
| Sodium nitrilotriacetate | 1.0 g |
| Sodium sulfite | 4.0 g |
| Sodium carbonate | 30.0 g |
| Potassium bromide | 1.4 g |
| Hydroxylamine sulfate | 2.4 g |
| 4-(N—Ethyl-N—β-hydroxyethylamino)-2-methylaniline sulfate | 4.5 g |
| Water to make | 1000 ml |
| Bleaching Solution | |
| Ammonium bromide | 160.0 g |
| Aqueous ammonia (28 wt %) | 25.0 ml |
| Sodium ethylenediaminetetraacetato | 130.0 g |
| Glacial acetic acid | 14.0 ml |
| Water to make | 1000 ml |
| Fixing Solution | |
| Sodium tetrapolyphosphate | 2.0 g |
| Sodium sulfite | 4.0 g |
| Ammonium thiosulfate aqueous solution (70 wt %) | 175.0 ml |
| Sodium bisulfite | 4.6 g |
| Water to make | 1.0 liter |
| Stabilizing Solution | |
| Formalin | 8.0 ml |
| Water to make | 1000 ml |

The results thus-obtained with each sample are shown in Table 5 below.

TABLE 5

| Sample | | Fog | Red Image Relative Sensitivity* | RMS Graininess** |
|---|---|---|---|---|
| 21 | (Comparison) | 0.14 | 100 | 0.048 |
| 22 | (Coupler (3) of the present invention) | 0.14 | 96 | 0.042 |
| 23 | (Coupler (17) of the present invention) | 0.13 | 92 | 0.041 |
| 24 | (Coupler (1) of the present invention) | 0.14 | 98 | 0.043 |

*Red Image Relative Sensitivity: The relative sensitivity is shown by a reciprocal of the exposure amount required for obtaining a density of fog + 0.2 and the sensitivity of Sample 21 is taken as 100.
**RMS Graininess: The value is obtained at 0.8 of image density

COMPOUNDS USED IN EXAMPLE 3
UV ray absorbent
Coupler
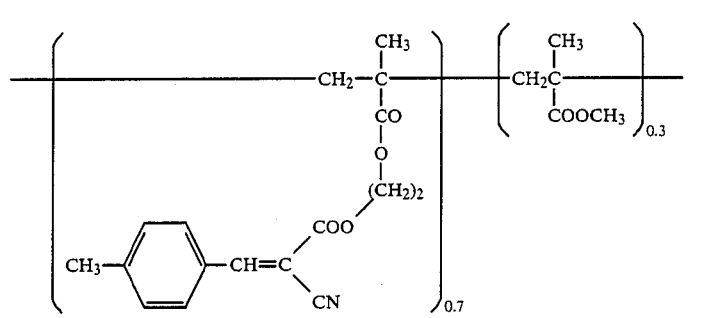
U-1
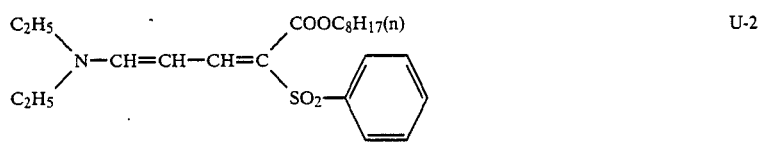
U-2
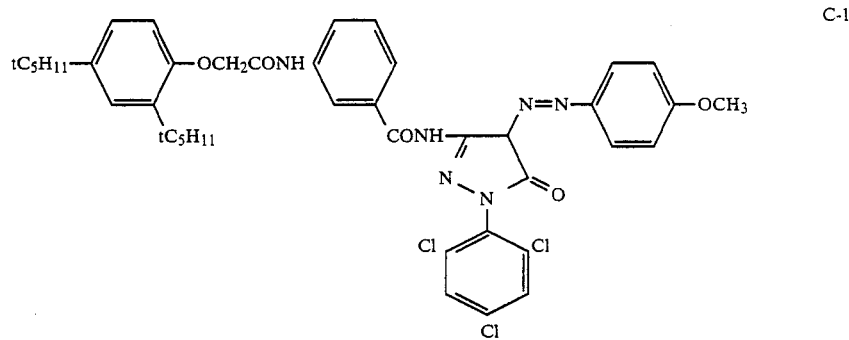
C-1
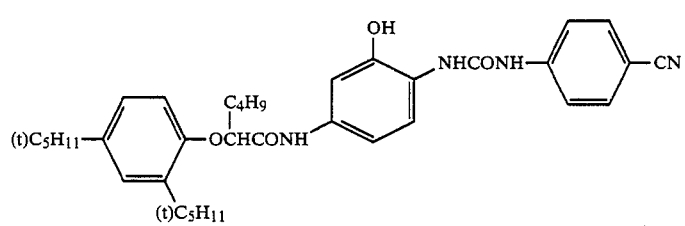
C-2
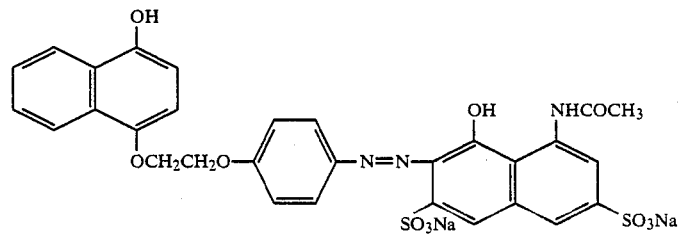
C-3

-continued
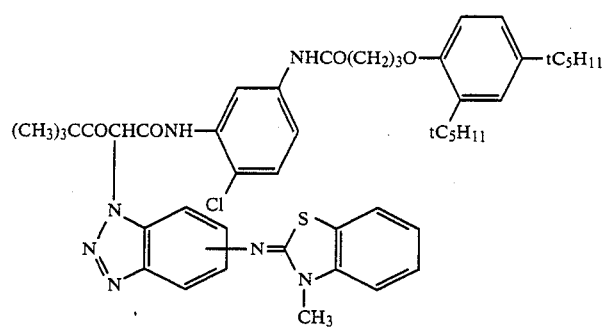
C-4
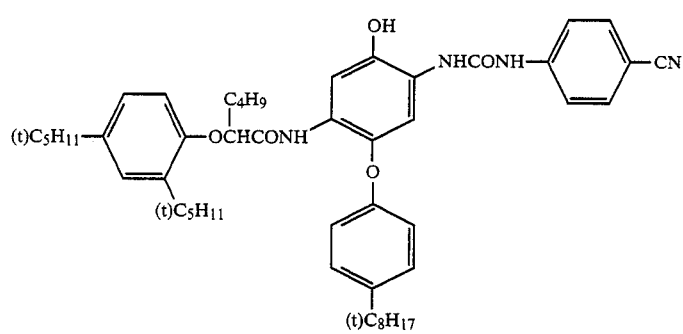
C-5
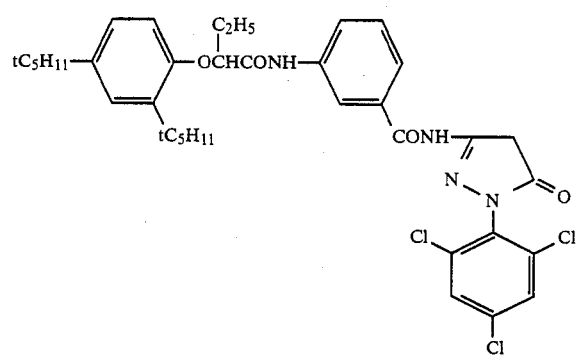
C-6
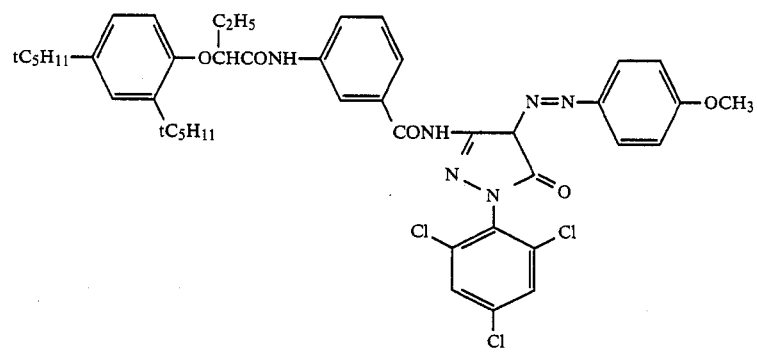
C-7

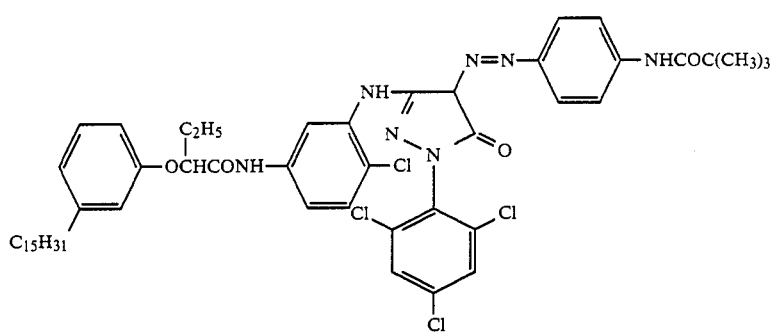
C-8
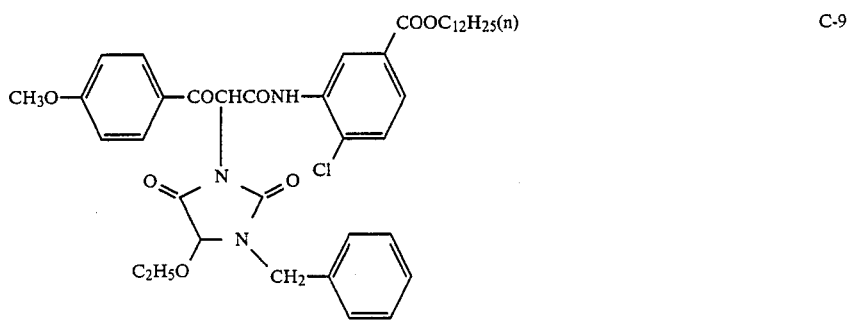
C-9
Sensitizing dye
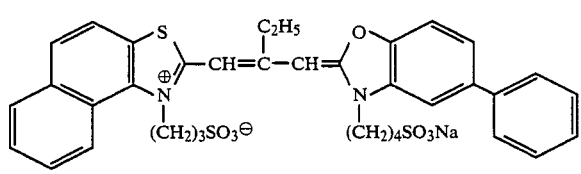
I
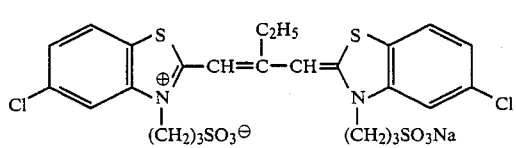
II
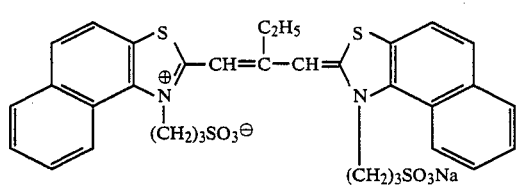
III
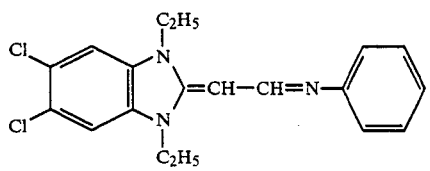
IV
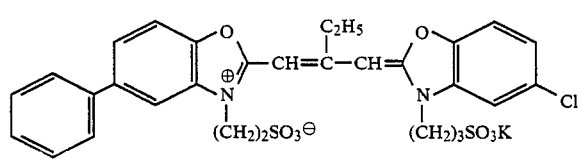
V

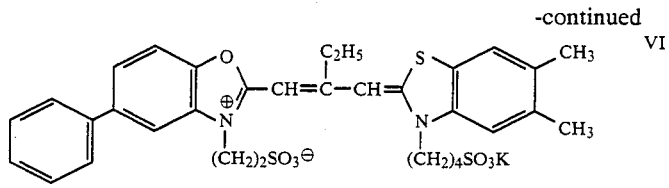
VI

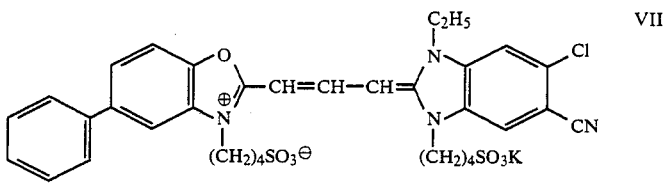
VII

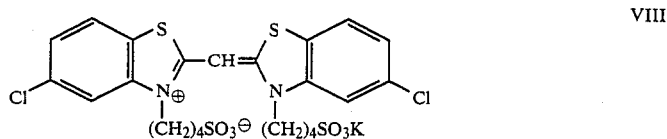
VIII

Gelatin hardening agent $CH_2=CH-SO_2-CH_2-CONH(CH_2)_2NHCO-CH_2-SO_2-CH=CH_2$  H-1

From the results of Table 5, it can be seen that the samples (Samples 22-24) of this invention have improved graininess as compared with the Sample 21 using a conventional coupler.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material containing at least one coupler represented by formula (I)

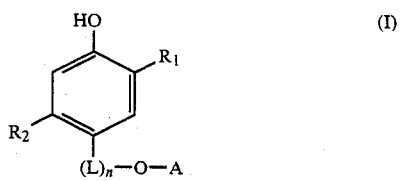

wherein $R_1$ represents a substituted or unsubstituted ureido group or a substituted or unsubstituted acylamino group; $R_2$ represents a substituted or unsubstituted acylamino group; L represents a group which is capable of being released from the phenolic group of formula (I) in a reaction with the oxidation product of a developing agent, and releases —O—A thereafter; n represents 0 or 1; and A represents an aromatic group substituted with a hydroxy group or a substituted amino group selected from the group consisting of an aliphatic amino group, an aromatic amino group, an acylamino group, a sulfonamido group, a carbmoylamino group, a sulfamoylamino group, an alkoxyamino group, a hydroxyamino group and an acyloxyamino group or an unsubstituted amino group at at least one of the 2-position and the 4-position thereof, wherein said silver halide color photographic material contains at least one other color image-forming coupler together with the coupler represented by formula (I), which at least one other color-image forming coupler is represented by formula (III)

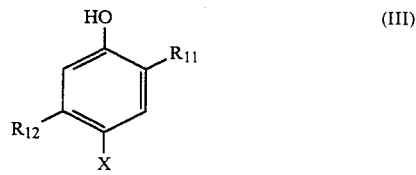

wherein $R_{11}$ represents a substituted or unsubstituted ureido group or a substituted or unsubstituted acylamino group; and $R_{12}$ represents a substituted or unsubstituted acylamino group; and X represents a hydrogen atom or a coupler releasable group.

2. A silver halide color photographic material as in claim 1, wherein the coupler represented by formula (I) exists in a red-sensitive silver halide emulsion layer of the color photographic material.

3. A silver halide color photographic material as in claim 2, wherein the coupler represented by formula (I) exists in the red-sensitive silver halide emulsion layer together with the at least one other color image forming coupler.

4. A silver halide color photographic material as in claim 2, wherein the ratio of the coupler represented by the general formula (I)/other color image-forming coupler is from 10/90 to 60/40.

5. A silver halide color photographic material as in claim 1, wherein X in formula (III) is a chlorine atom, an aromatic oxy group, or an aliphatic oxy group.

6. A silver halide color photographic material comprising a support having thereon at least one red-sensitive emulsion layer, at lest one green-sensitive emulsion layer, and at least one blue-sensitive emulsion layer, said red-sensitive emulsion layer containing at least one coupler represented by formula (I)

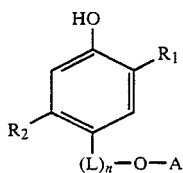

wherein $R_1$ represents a substituted or unsubstituted ureido group or a substituted or unsubstituted acylamino group; $R_2$ represents a substituted or unsubstituted acylamino group; L represents a group capable of being released from the phenolic group of formula (I) in a reaction with the oxidation product of a developing agent, and releases —O—A thereafter; n represents 0 or 1; and A represents an aromatic group substituted by a hydroxy group or a substituted amino group related from the group consisting of an aliphatic amino group, an aromatic amino group, an acylamino group, a sulfonamido group, a carbmoylamino group, a sulfamoylamino group, an alkoxyamino group, a hydroxyamino group and an acyloxyamino group or an unsubstituted amino group at at least one of the 2-position and the 4-position thereof, wherein said silver halide color photographic material contains at least one other color image-forming coupler together with the coupler represented by formula (I), which at least one other color-image forming coupler is represented by formula (III)

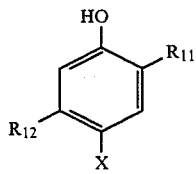

wherein $R_{11}$ represents a substituted or unsubstituted ureido group or a substituted or unsubstituted acylamino group; and $R_{12}$ represents a substituted or unsubstituted acylamino group; and X represents a hydrogen atom or a coupler releasable group.

7. A silver halide color photographic material as in claim 6, wherein the coupler represented by formula (I) exists in the red-sensitive emulsion layer together with the at least one other color image-forming coupler.

8. A silver halide color photographic material as in claim 7, wherein the ratio of the coupler represented by formula (I)/other color image-forming coupler is from 10/90 to 60/40.

9. A silver halide color photographic material as in claim 1, wherein $R_1$ represents a substituted ureido group and said $R_1$ of formula (I) is represented by formula (II-a) or (II-b)

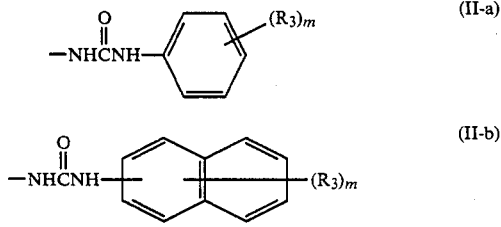

wherein $R_3$ represents an aliphatic group, an aromatic group, a halogen atom, an alkoxy group, an aryloxy group, an acylamino group, an alkoxycarbonyl group, an aryloxycarbonyl group, a cyano group, a nitro group, a sulfonyl group, a sulfamoyl group, a carbamoyl group, a ureido group, a carboxyl group, a hydroxyl group, a nitroso group, an alkylthio group, an arylthio group, an acyl group, a sulfonamido group, an acyloxy group, a heterocyclic group, an alkoxycarbonylamino group, an oxamoyl group, a thioacyl group, an acylcarbamoyl group, a sulfinyl group, a thioureido group, a thiocarbamoyl group, a diacylamino group, or an amino group; m represents an integer of 0 to 5, and when m is 2 or more, the $R_3$ groups can be the same or different.

10. A silver halide color photographic material as in claim 1, wherein $R_1$ or $R_2$ represents an aliphatic or aromatic acylamino group.

11. A silver halide color photographic material as in claim 10, wherein $R_1$ or $R_2$ is an aliphatic acylamino group and the number of carbon atoms of the group is from 1 to 32.

12. A silver halide color photographic material as in claim 11, wherein the aliphatic acylamino group is a cyclic or non-cyclic group, a straight chain or branched chain group, a saturated or unsaturated group, and a substituted or unsubstituted group.

13. A silver halide color photographic material as in claim 12, wherein the substituents for the substituted group are a halogen atom, an aryloxy group, an arylthio group, an aryloxycarbonyl group, an alkoxycarbonyl group, an acyloxy group, an acylamino group, a sulfonamido group, a hydroxyl group, a carbonyl group, a cyano group, an aryl group, an alkoxy group, an alkylthio group, a carbamoyl group, and a ureido group.

14. A silver halide color photographic material as in claim 10, wherein $R_1$ or $R_2$ is an aromatic acylamino group and the number of carbon atoms of the group is from 6 to 10.

15. A silver halide color photographic material as in claim 14, wherein the aromatic acylamino group is a substituted or unsubstituted phenyl group.

16. A silver halide color photographic material as in claim 15, wherein the substituent for the substituted phenyl group are a halogen atom, a sulfonamido group, an alkoxy group, an alkoxycarbonyl group, an aliphatic group, an aryl group, a cyano group, a sulfonyl group, a sulfamoyl group, an acylamino group, a hydroxy group, an alkylthio group, a carbamoyl group, a carboxy group, and a ureido group.

17. A silver halide color photographic material as in claim 1, wherein the connecting group represented by L in formula (I) are a group capable of being cleaved by an intramolecular nucleophilic substitution reaction after being released from the coupler, a group capable of being cleaved by an electron transfer through a covalent bond, a methyleneoxy group, a oxycarbonyloxy group, and a group capable of being cleaved by an electron transfer through a sigma ($\sigma$) bond.

18. A silver halide color photographic material as in claim 6 wherein the connecting group represented by L in formula (I) are a group capable of being cleaved by an intramolecular nucleophilic substitution reaction after being released from the coupler, a group capable of being cleaved by an electron transfer through a covalent bond, a methyleneoxy group, a oxycarbonyloxy group, and a group capable of being cleaved by an electron transfer through a sigma ($\sigma$) bond.

19. A silver halide color photographic light-sensitive material as in claim 6, wherein $R_1$ represents a substituted ureido group and said $R_1$ of formula (I) is represented by formula (II-a) or (II-b)

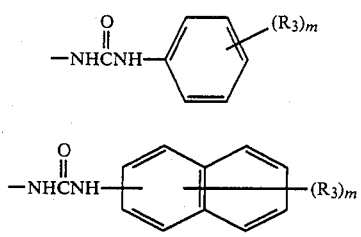

wherein $R_3$ represents an aliphatic group, an aromatic group, a halogen atom, an alkoxy group, an aryloxy group, an acylamino group, an alkoxycarbonyl group, an acylamino group, an alkoxycarbonyl group, an aryloxycarbonyl group, a cyano group, a nitro group, a sulfonyl group, a sulfamoyl group, a carbamoyl group, a ureido group, a carboxyl group, a hydroxyl group, a nitroso group, an alkylthio group, an arylthio group, an acyl group, a sulfonamido group, an acyloxy group, a heterocyclic group, an alkoxycarbonylamino group, an oxamoyl group, a thioacyl group, an acylcarbamoyl group, a sulfinyl group, a thioureido group, a thiocarbamoyl group, a diacylamino group, or an amino group; m represents an integer of 0 to 5, and when m is 2 or more, the $R_3$ groups can be the same or different.

20. A silver halide color photographic material as in claim 3, wherein the ratio of the coupler represented by formula (I)/other color image-forming couplers is from 10/90 to 60/40.

21. A silver halide color photographic light-sensitive material as in claim 7, wherein the ratio of the coupler represented by formula (I)/other color image-forming couplers is from 10/90 to 60/40.

22. A silver halide color photographic material as in claim 1, wherein the substituents at at least one of the 2-position and the 4-position of A are selected from a hydroxy group and a sulfonamido group.

23. A silver halide color photographic material as in claim 6, wherein the substituents at at least one of the 2-position and the 4-position of A are selected from a hydroxy group and a sulfonamido group.

24. A silver halide color photographic material as in claim 1, wherein the substituted amino group on A is an aliphatic amino group and it has from 1 to 8 carbon atoms.

25. A silver halide color photographic material as in claim 6, wherein the substituted amino group on A is an aliphatic amino group and it has from 1 to 8 carbon atoms.

26. A silver halide color photographic material as in claim 1, wherein when the substituent on A is an aromatic amino group and it has from 6 to 10 carbon atoms.

27. A silver halide color photographic material as in claim 6, wherein when the substituent on A is an aromatic amino group and it has from 6 to 10 carbon atoms.

28. A silver halide color photographic material as in claim 1, wherein A is substituted at both the 2-position and the 4-position thereof.

29. A silver halide color photographic material as in claim 6, wherein A is substituted at both the 2-position and the 4-position thereof.

30. A silver halide color photographic material as in claim 1, wherein —O—A after release causes an oxidation-reduction reaction with the oxidation product of a developing agent.

31. A silver halide color photographic material as in claim 6, wherein —O—A after release causes an oxidation-reduction reaction with the oxidation product of a developing agent.

* * * * *